US012357769B2

(12) United States Patent
Jensen

(10) Patent No.: US 12,357,769 B2
(45) Date of Patent: Jul. 15, 2025

(54) NEEDLE SHIELD REMOVERS, DRUG DELIVERY DEVICES, AND RELATED METHODS

(71) Applicant: AMGEN INC., Thousand Oaks, CA (US)

(72) Inventor: Jan Jensen, Copenhagen (DK)

(73) Assignee: AMGEN INC., Thousand Oaks, CA (US)

(*) Notice: Subject to any disclaimer, the term of this patent is extended or adjusted under 35 U.S.C. 154(b) by 103 days.

(21) Appl. No.: 17/134,630

(22) Filed: Dec. 28, 2020

(65) Prior Publication Data

US 2021/0213210 A1     Jul. 15, 2021

Related U.S. Application Data

(60) Provisional application No. 62/960,463, filed on Jan. 13, 2020.

(51) Int. Cl.
*A61M 5/32* (2006.01)
*A61M 5/20* (2006.01)
*A61M 5/24* (2006.01)

(52) U.S. Cl.
CPC ............ *A61M 5/3204* (2013.01); *A61M 5/20* (2013.01); *A61M 5/2033* (2013.01); *A61M 5/24* (2013.01);
(Continued)

(58) Field of Classification Search
CPC ........ A61M 5/3204; A61M 5/20; A61M 5/24; A61M 5/2033; A61M 2005/3247;
(Continued)

(56) References Cited

U.S. PATENT DOCUMENTS 2,855,252 A * 10/1958 Budinger ................ F16C 33/14
29/521
6,634,076 B2 * 10/2003 Hjertman .............. F16L 25/009
138/120
(Continued)

FOREIGN PATENT DOCUMENTS

EP         2739329 B2     9/2020
WO      2014146210 A1    9/2014
(Continued)

OTHER PUBLICATIONS

Elizabeth A. Killion et al. ,Anti-obesity effects of GIPR antagonists alone and in combination with GLP-1R agonists in preclinical models. Sci. Transl. Med. 10,eaat3392(2018). DOI:10.1126/scitranslmed.aat3392 (Year: 2018).*
(Continued)

*Primary Examiner* — Tasnim Mehjabin Ahmed

(57) ABSTRACT

Needle shield removers, drug delivery devices, and associated methods are provided that include a tubular body formed from a sheet with a closure having from a plurality of teeth extending laterally outwardly from one longitudinal edge of the sheet and a plurality of grooves extending laterally inwardly into the sheet of material from a second longitudinal edge of the sheet. The plurality of teeth are frictionally received within the plurality of grooves to thereby hold the body in a tubular configuration. The needle shield removers can further include a first plurality of barbs arrayed around a circumference of the body adjacent to a first end thereof and a second plurality of barbs arrayed around a circumference of the body adjacent to a second end thereof.

20 Claims, 13 Drawing Sheets

(52) U.S. Cl.
CPC .............. *A61M 2005/2013* (2013.01); *A61M 2005/3247* (2013.01); *A61M 2005/3267* (2013.01)

(58) Field of Classification Search
CPC .. A61M 2005/3267; A61M 2005/2013; B21D 39/02; B21D 39/03; B21D 39/031
See application file for complete search history.

(56) References Cited

U.S. PATENT DOCUMENTS

| | | | |
|---|---|---|---|
| 9,339,610 | B2 | 5/2016 | Julian et al. |
| 10,583,255 | B2 | 3/2020 | Maxfield |
| 10,814,074 | B2 | 10/2020 | Taal et al. |
| 10,918,803 | B2 | 2/2021 | Kemp et al. |
| 11,027,068 | B2 | 6/2021 | Mosebach et al. |
| 11,077,257 | B2 | 8/2021 | Kemp |
| 11,318,252 | B2 | 5/2022 | Zhang |
| 11,369,750 | B2 | 6/2022 | Taal et al. |
| 2001/0020491 | A1* | 9/2001 | Kondou ............... B21D 39/037 138/156 |
| 2014/0288503 | A1* | 9/2014 | Julian ..................... A61M 5/20 29/428 |
| 2014/0343503 | A1* | 11/2014 | Holmqvist .......... A61M 5/3204 81/3.4 |
| 2016/0296713 | A1* | 10/2016 | Schader .............. A61M 5/3245 |
| 2018/0369495 | A1* | 12/2018 | Stewart ................ A61M 5/3202 |
| 2019/0201634 | A1* | 7/2019 | Newton ............... A61M 5/3213 |
| 2020/0094302 | A1* | 3/2020 | Yahagi .................. B21C 37/104 |
| 2021/0077743 | A1 | 3/2021 | Kemp et al. |
| 2021/0299356 | A1 | 9/2021 | Cereda et al. |
| 2021/0338940 | A1 | 11/2021 | Kemp et al. |
| 2021/0353862 | A1 | 11/2021 | Schrul et al. |
| 2022/0008661 | A1 | 1/2022 | Kemp |

FOREIGN PATENT DOCUMENTS

| | | |
|---|---|---|
| WO | 2016193341 A1 | 12/2016 |
| WO | 2016193374 A1 | 12/2016 |
| WO | 2017223354 A1 | 12/2017 |
| WO | 2018167491 A1 | 9/2018 |
| WO | WO-2019/101613 A1 | 5/2019 |

OTHER PUBLICATIONS

International Application No. PCT/US2020/067118, International Search Report and Written Opinion, mailed Apr. 16, 2021.
Office Action received in counterpart Japanese Patent Application No. 2022-542167, dated Oct. 1, 2024.
Second Office Action received in counterpart Japanese Patent Application No. 2022-542167, dated Feb. 4, 2025.
Examination report received in counterpart European Patent Application No. 20848744.7, dated Apr. 10, 2025.

* cited by examiner

NEEDLE SHIELD REMOVERS, DRUG DELIVERY DEVICES, AND RELATED METHODS

Priority is claimed to U.S. Provisional Patent Application No. 62/960,463, filed Jan. 13, 2020, and the entire contents thereof are hereby incorporated herein by reference.

FIELD OF THE DISCLOSURE

The present disclosure relates to drug delivery devices, and, more particularly, devices for automatically injecting a drug into a patient.

BACKGROUND

A general aversion to exposed needles, as well as health and safety issues, have led to the development of drug delivery devices which conceal a needle or other insertion member prior to use and which automate various aspects of an injection process. Such devices offer a variety of benefits as compared with traditional forms of drug delivery including, for example, delivery via a conventional syringe.

A drug delivery device may incorporate various mechanisms to implement various automated features. Such features include automatically covering a needle in a pre-delivery and/or post-delivery state, providing an interface for a user to activate a drive mechanism, indicating to the user that drug delivery is complete, among other features. Typically a drug delivery device will incorporate a separate or independently operable mechanism to realize each of its automated features. As a consequence, with each added feature, the mechanical complexity of the device tends to increase. This, in turn, can increase the size of the device, which can make it cumbersome for the user to handle, as well as increase manufacturing costs and timeframes. As the demand grows for drug delivery devices with greater ease of use and safety, finding a way to incorporate more automated features without adding undue complexity to the drug delivery device presents various design and manufacturing challenges.

The present disclosure sets forth drug delivery devices embodying advantageous alternatives to existing drug delivery devices, and that may address one or more of the challenges or needs mentioned herein.

SUMMARY

In accordance with a first aspect, a needle shield remover is described that includes a body having a tubular configuration with first and second ends, where the body is formed from a sheet of material having opposing first and second longitudinal edges. The needle shield remover further includes a closure configured to couple the first and second longitudinal edges together to form the tubular configuration of the body. The closure includes a plurality of teeth extending laterally outwardly from the first longitudinal edge and a plurality of grooves extending laterally inwardly into the sheet of material from the second longitudinal edge.

In some forms, the needle shield remover can include a first plurality of barbs arrayed around a circumference of the body adjacent to the first end and a second plurality of barbs arrayed around a circumference of the body adjacent to the second end. In further forms, each of the first plurality of barbs and the second plurality of barbs can extend within an opening of the body and include a distal end having laterally spaced pointed tips and/or the first plurality of barbs and the second plurality of barbs can extend inwardly into the body.

In some forms, the plurality of teeth can extend generally perpendicularly away from the first longitudinal edge; and the plurality of grooves can extend along axis at an angle with respect to the second longitudinal edge, such that the plurality of teeth bend as each respective tooth enters a respective one of the plurality of grooves. In further forms, each of the plurality of teeth can include an associated cut-out portion configured to relieve stress within the material as a result of the plurality of teeth bending. In some examples, the cut-out portion can be disposed in an edge of each of the plurality of teeth or in a corner between each of the plurality of teeth and the first longitudinal edge. In additional forms, the plurality of grooves can extend along an axis at an angle of between 5 degrees and 20 degrees with respect to the second longitudinal edge and/or the axes of the plurality of grooves can be staggered to extend above or below a horizontal line extending between the first and second longitudinal edges.

In accordance with a second aspect, an auto-injector drug delivery device is described that includes a housing, a drug container coupled to the housing, where the drug container includes a needle, a needle shield disposed at least partially over a distal end of the needle of the drug container, and a removable cap coupled to the housing. The auto-injector drug delivery device further includes a needle shield remover that is coupled to the removable cap and the needle shield, such that uncoupling the removable cap from the housing removes the needle shield off the needle of the drug container. The needle shield remover includes a body having a tubular configuration with first and second ends, the body formed from a sheet of material having opposing first and second longitudinal edges and a closure coupling the first and second longitudinal edges together to form the tubular configuration of the body. The closure includes a plurality of teeth that extend laterally outwardly from the first longitudinal edge and a plurality of grooves that extend laterally inwardly into the sheet of material from the second longitudinal edge, where the plurality of grooves receive the plurality of teeth to couple the first and second longitudinal edges together.

In some forms, the needle shield remover can include a first plurality of barbs arrayed around a circumference of the body adjacent to the first end and a second plurality of barbs arrayed around a circumference of the body adjacent to the second end, where the first plurality of barbs grip the removable cap and the second plurality of barbs grip the needle shield. In further forms, each of the first plurality of barbs and the second plurality of barbs can extend within an opening of the body and include a distal end having laterally spaced pointed tips and/or the first plurality of barbs and the second plurality of barbs can extend inwardly into the body.

In some forms, the removable cap can include a central wall configured to be gripped by the first plurality of barbs and, in further forms, an annular wall spaced outwardly from the central wall configured to engage an outer surface of the first end of the body.

The closure of these forms can have a configuration according to any of the above configurations. Additionally, the needle shield remover of any of the above forms can be symmetrical about a horizontal plane extending through a midpoint of the body perpendicular to a longitudinal axis thereof.

In accordance with a third aspect, a method of forming a needle shield remover from a strip of metal is described that includes forming a sheet from the strip of metal having first and second longitudinal edges and end edges, where the sheet includes a closure for the needle shield remover including a plurality of teeth extending laterally outwardly from the first longitudinal edge and a plurality of grooves extending laterally inwardly into the sheet of material from the second longitudinal edge. The method further includes forming a first plurality of barbs across a width of the strip of metal, forming a second plurality of barbs across the width of the strip of metal, and creating a tubular form from the sheet by forcing the plurality of teeth into the plurality of grooves.

In some forms, the plurality of teeth can extend generally perpendicularly away from the first longitudinal edge, the plurality of grooves can extend along axis at an angle with respect to the second longitudinal edge, and the method can include creating the tubular form from the sheet comprises bending the plurality of teeth as each respective tooth enters a respective one of the plurality of grooves.

In some forms, the method can include punching guide holes into the trip of metal to form a cutting pattern for the closure, the first plurality of barbs, and the second plurality of barbs.

DETAILED DESCRIPTION

The present disclosure generally relates to drug delivery devices operable by a user for administering a drug, or in the case where a patient is the user, self-administering a drug. Various features are disclosed to facilitate safe and proper handling of the drug delivery device, including handling the drug delivery device after it has been used to deliver its payload. Such features include, but are not limited to, an indicator for signaling to the user that drug delivery is complete and a drive mechanism activatable by pressing the drug delivery device against the patient's skin at the injection site. These features and others work together and/or interact with one another in synergistic ways so as to limit the number of moving parts and/or complexity of the drug delivery device. Furthermore, certain features described herein exploit a biasing force exerted by a plunger biasing member and/or a guard biasing member for actuation purposes, thereby reducing any force that must be applied by the user and/or alleviating a need to incorporate a dedicated energy source for implementing said feature. These and other advantages will be apparent to one of ordinary skill in the art reviewing the present disclosure.

Figure 1:
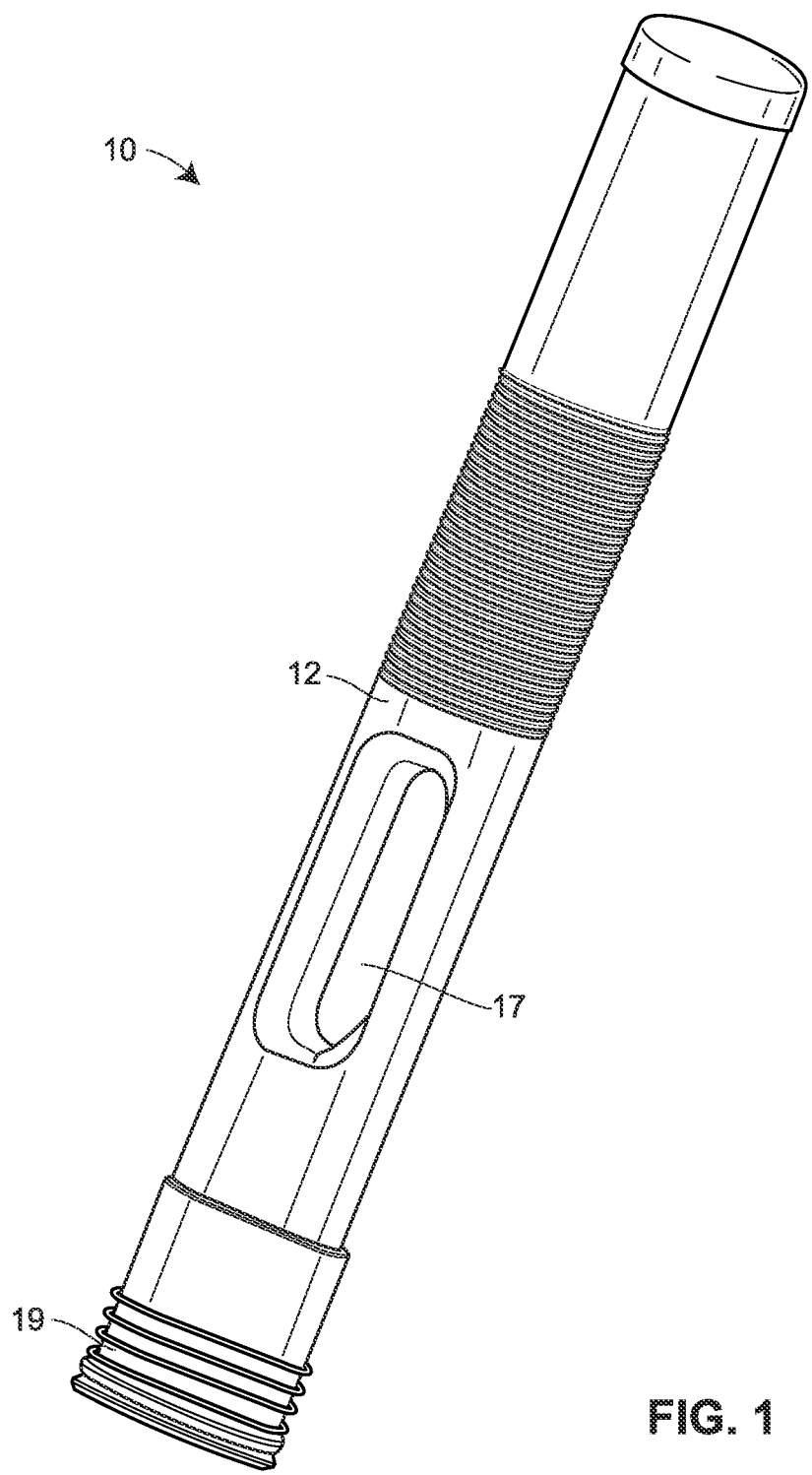
FIG. 1 is a perspective view of a drug delivery device according to various embodiments of the present disclosure.
Figure 2:
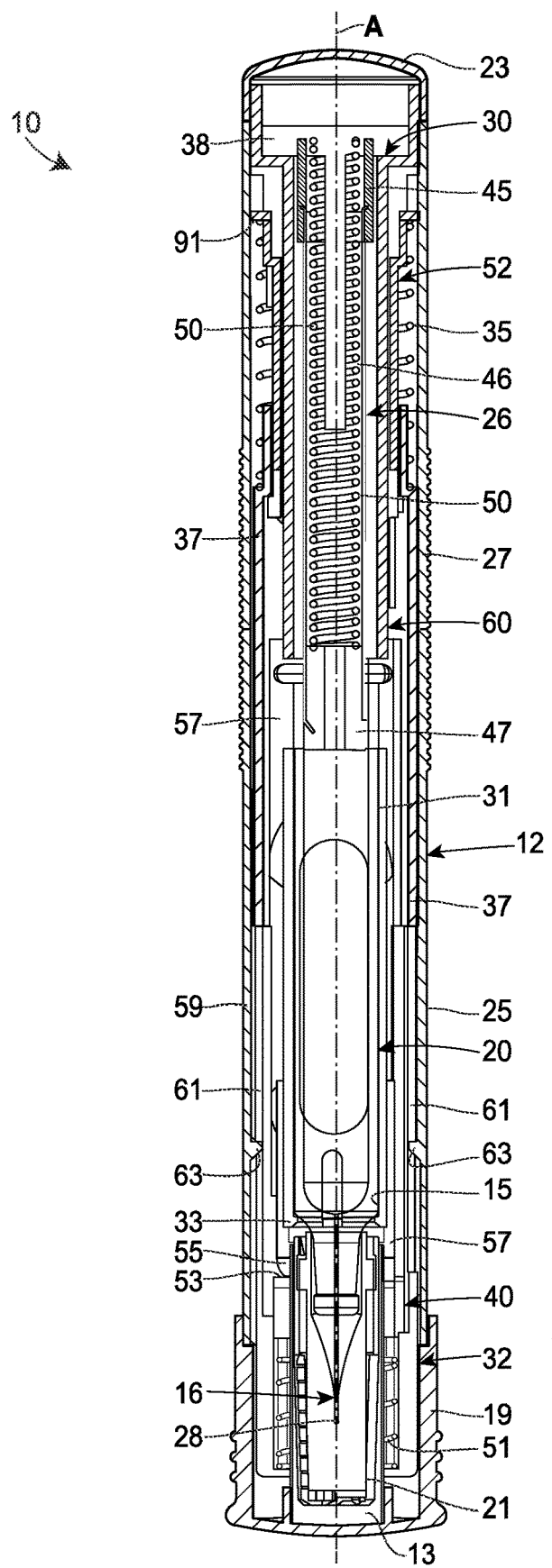
FIG. 2 is cross-sectional view of the drug delivery device in FIG. 1.
Figure 3:
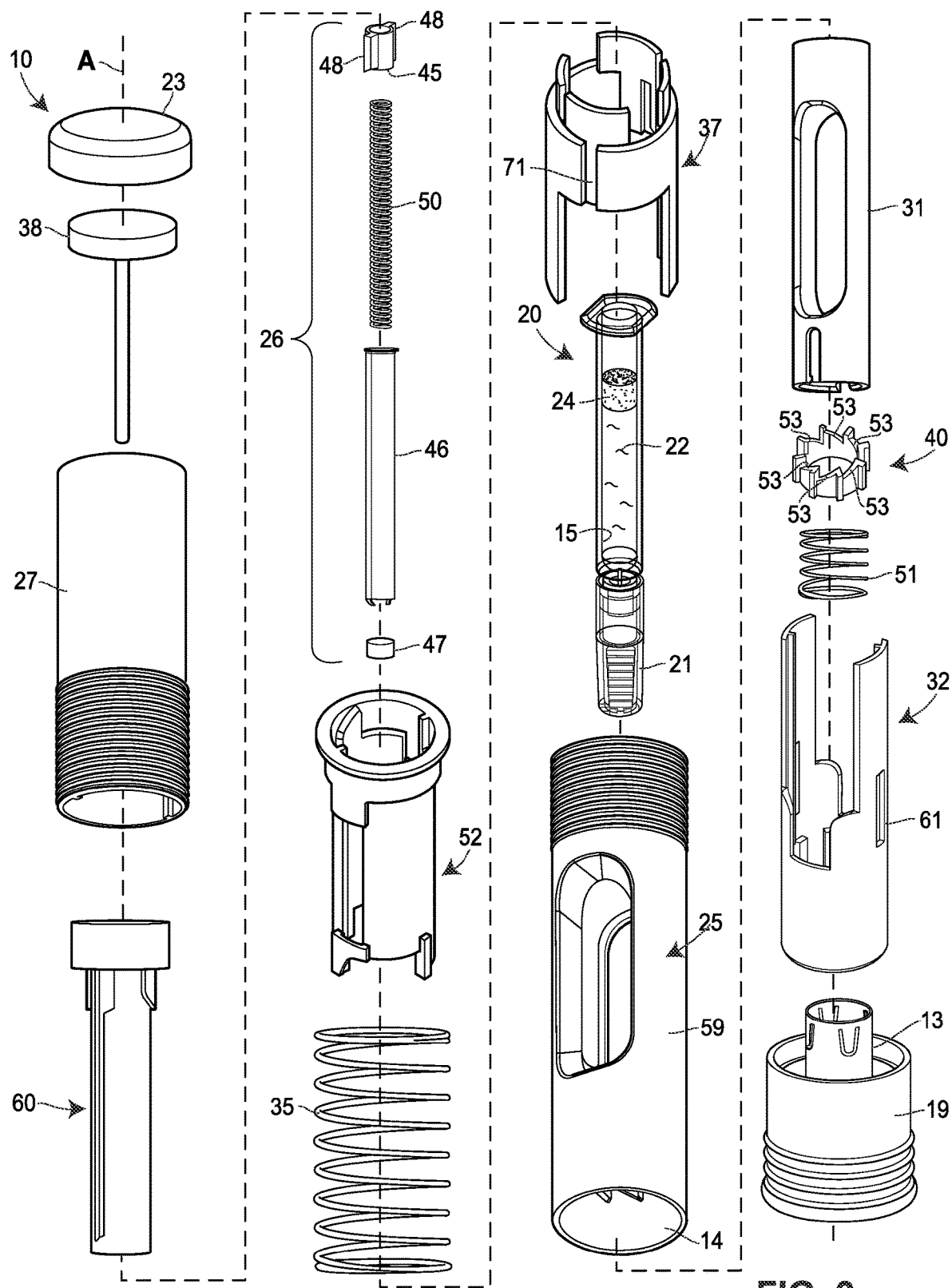
FIG. 3 is an exploded assembly view of the drug delivery device in FIG. 2.
Figure 4:
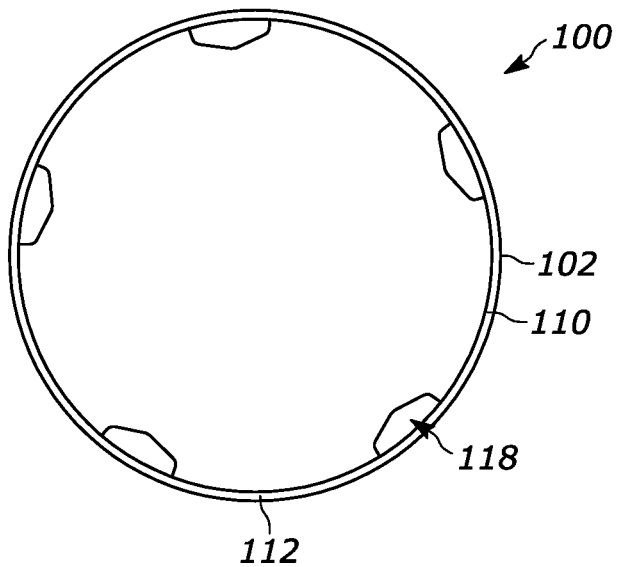
FIG. 4 is a side elevational view of an example needle shield remover according to various embodiments of the present disclosure.

FIGS. 1-3 illustrate several views of an embodiment of a drug delivery device 10 for delivering a drug, which may also be referred to herein as a medicament or drug product. The drug may be, but is not limited to, various biologicals such as peptides, peptibodies, or antibodies. The drug may be in a fluid or liquid form, although the disclosure is not limited to a particular state.

Various implementations and configurations of the drug delivery device 10 are possible. The present embodiment of the drug delivery device 10 is configured as a single-use, disposable injector. In other embodiments, the drug delivery device 10 may be configured as multiple-use reusable injector. The drug delivery device 10 is operable for self-administration by a patient or for administration by caregiver or a formally trained healthcare provider (e.g., a doctor or nurse). The present embodiment of the drug delivery device 10 takes the form of an autoinjector or pen-type injector, and, as such, may be held in the hand of the user over the duration of drug delivery.

The configuration of various components included in the drug delivery device 10 may depend on the operational state of the drug delivery device 10. The drug delivery device 10 may have a pre-delivery or storage state, a delivery or dosing state, and a post-delivery state, although fewer or more states are also possible. The pre-delivery state may correspond to the configuration of the drug delivery device 10 subsequent to assembly and prior to activation by the user. In some embodiments, the pre-delivery state may exist in the time between when the drug delivery device 10 leaves a manufacturing facility and when a patient or user activates a drive mechanism 30 of the drug delivery device 10. This includes the moments in time after the user has removed the drug delivery device 10 from any secondary packaging and prior to positioning the drug delivery device 10 against the injection site. The delivery state may correspond to the configuration of the drug delivery device 10 while drug delivery, also referred to herein as dosing, is in progress. The post-delivery state may correspond to the configuration of the drug delivery device 10 after drug delivery is complete and/or when a stopper is arranged in an end-of-dose position in a drug storage container.

The drug delivery device 10 includes an outer casing or housing 12. In some embodiments, the housing 12 may be sized and dimensioned to enable a person to grasp the injector 10 in a single hand. The housing 12 may have a generally elongate shape, such as a cylindrical shape, and extend along a longitudinal axis A between a proximal end and a distal end. An opening 14 may be formed in the distal end to permit an insertion end 28 of a delivery member 16 to extend outside of the housing 12. A transparent or semi-transparent inspection window 17 may be positioned in a wall of the housing 12 to permit a user to view component (s) inside the drug delivery device 10, including a drug storage container 20. Viewing the drug storage container 20 through the window 17 may allow a user to confirm that drug delivery is in progress and/or complete. A removable cap 19 may cover the opening 14 prior to use of the drug delivery device 10, and, in some embodiments, may including a gripper 13 configured to assist with removing a sterile barrier 21 (e.g., a rigid needle shield (RNS), a flexible needle shield (FNS), etc.) mounted on the insertion end 28 of the delivery member 16. The gripper 13 may include one or more inwardly protruding barbs or arms that frictionally or otherwise mechanically engage the sterile barrier 21 to pull the sterile barrier 21 with the removable cap 19 when the user separates the removable cap 19 from the housing 12. Thus, removing the removable cap 19 has the effect of removing the sterile barrier 21 from the delivery member 16.

In the present embodiment, the housing 12 is defined by three separate and interconnected structures: a rear end cap 23 at the proximal end of the drug delivery device 10; a front housing 25 at the distal end of the drug delivery device 10 and which includes the opening 14; and a rear housing 27 positioned between and rigidly connecting the rear end cap 23 and the front housing 25. The front housing 25 and the rear housing 27 each may have a hollow and generally cylindrical or tubular shape, and the rear end cap 23 may have a generally hemispherical shape or a hollow cylindrical shape with an open end and a closed off end. In some embodiments, the rear end cap 23 and the rear housing 27, and any components to be positioned therein, may be assembled together to define a rear sub-assembly. Meanwhile the front housing 25 and any components to be positioned therein may be assembled together to define a front sub-assembly. In some embodiments, the rear and front sub-assemblies are assembled independently of each other and then later combined with one another, as well as with the drug storage container 20, to form the fully-assembled drug delivery device 10. In certain such embodiments, some or all of the foregoing phases of assembly may occur in different manufacturing facilities or environments. In alternative embodiments, the housing 12 may be constructed in one piece, such that the housing 12 is defined by a single, monolithic structure.

The drug storage container 20 is disposed within an interior space of the housing 12 and is configured to contain a drug 22. The drug storage container 20 may be pre-filled and shipped, e.g., by a manufacturer, to a location where the drug storage container 20 is combined with a remainder of the drug delivery device 10. The housing 12 may be pre-loaded with the drug storage container 20, e.g., by a manufacturer, or alternatively, loaded with the drug storage container 20 by a user prior to use of the drug delivery device 10. The drug storage container 20 may include a rigid wall defining an internal bore or reservoir. The wall may be made of glass or plastic. A stopper 24 may be moveably disposed in the drug storage container 20 such that it can move in a distal direction along the longitudinal axis A between proximal end and a distal end of the drug storage container 20. The stopper 24 may be constructed of rubber or any other suitable material. The stopper 24 may slidably and sealingly contact an interior surface 15 of the wall of the drug storage container 20 such that the drug 22 is prevented or inhibited from leaking past the stopper 24 when the stopper 24 is in motion. Distal movement of the stopper 24 expels the drug 22 from the reservoir of the drug storage container 20 into the delivery member 16. The proximal end of the drug storage container 20 may be open to allow a plunger 26 to extend into the drug storage container 20 and push the stopper 24 in the distal direction. In the present embodiment, the plunger 26 and the stopper 24 are initially spaced from each other by a gap. Upon activation of a drive mechanism 30, the plunger 26 moves in the distal direction to close the gap and comes into contact with the stopper 24. Subsequent distal movement of the plunger 26 drives the stopper 24 in the distal direction to expel the drug 22 from the drug storage container 20. In alternative embodiments, the stopper 24 and the plunger 26 may initially be in contact with one another or coupled to one another, e.g., via a threaded coupling, such that they move together jointly from the start of movement of the plunger 26. Once the stopper 24 is in motion, it may continue to move in the distal direction until it contacts a proximally-facing portion of the interior surface 15 of the wall of the drug storage container 20. This position of the stopper 24 may be referred to as the end-of-dose or end-of-delivery position, and may correspond to when delivery of the drug 22 to the patient is complete or substantially complete.

In some embodiments, a volume of the drug 22 included in the reservoir of the drug storage container 20 may be equal to 1 mL, or equal to approximately (e.g., ±10%) 1 mL, or equal to 2.5 mL, or equal to approximately (e.g., ±10%) 2.5 mL, or less than or equal to approximately (e.g., ±10%) 2 mL, or less than or equal to approximately (e.g., ±10%) 3 mL, or less than or equal to approximately (e.g., ±10%) 4 mL, or less than approximately (e.g., ±10%) 5 mL, or less than or equal to approximately (e.g., ±10%) 10 mL, or within a range between approximately (e.g., 10%) 1-10 mL, or within a range between approximately (e.g., ±10%) 1-5 mL, or within a range between approximately (e.g., ±10%) 1-4 mL, or within a range between approximately (e.g., ±10%) 1-3 mL, or within a range between approximately (e.g., ±10%) 1-2.5 mL.

The delivery member 16 is connected or operable to be connected in fluid communication with the reservoir of the drug storage container 20. A distal end of the delivery member 16 may define the insertion end 28 of the delivery member 16. The insertion end 28 may include a sharpened tip of other pointed geometry allowing the insertion end 28 to pierce the patient's skin 5 and subcutaneous tissue during insertion of the delivery member 16. The delivery member 16 may be hollow and have an interior passageway. One or more openings may be formed in the insertion end 28 to allow drug to flow out of the delivery member 16 into the patient.

In the present embodiment, the drug storage container 20 is a pre-filled syringe and has a staked, hollow metal needle for the delivery member 16. Here, the needle is fixed relative to the wall of the drug storage container 20 and is in permanent fluid communication with the reservoir of the drug storage container 20. In other embodiments, the drug storage container 20 may be a needle-less cartridge, and, as such, initially may not be in fluid communication with the delivery member 16. In such embodiments, the drug storage container 20 may move toward a proximal end of the delivery member 16, or vice versa, during operation of the drug delivery device 10 such that the proximal end of the delivery member 16 penetrates through a septum covering an opening in the drug storage container 20 thereby establishing fluid communication between the reservoir of the drug storage container 20 and the delivery member 16.

The drug storage container 20 may be fixed relative to the housing 12 such that the drug storage container 20 does not move relative to the housing 12 once installed in the housing 12. As such, the insertion end 28 of the delivery member 16 extends permanently through the opening 14 in the housing 12 in the pre-delivery, delivery, and post-delivery states. In the present embodiment, a container holder 31 fixes the position of the drug storage container 20 within the housing 12. The container holder 31 may have a hollow and generally cylindrical or tubular shape, and the drug storage container 20 may be disposed partially or entirely within the container holder 31. A distal end of the container holder 31 may include an inwardly protruding flange 33 abutting against a neck of the drug storage container 20, thereby preventing distal movement of the drug storage container 20. The container holder 31 may be fixedly attached to the housing 12 such that the container holder 31 is prevented from moving relative to the housing 12 during operation of the drug delivery device 10.

In alternative embodiments, the drug storage container 20 may be moveably coupled to the housing 12 such that the drug storage container 20 is able to move relative to the housing 12 during operation of the drug delivery device 10. In certain such alternative embodiments, the insertion end 28 of the delivery member 16 may be retracted within the opening 14 in the housing 12 in the pre-delivery state. Subsequently, during operation of the injection device 10, the insertion end 28 of the delivery member 16 may be deployed through the opening 14 in the housing 12 for insertion into the patient. This motion may, in some embodiments, be the result of the drug storage container 20 having been driven in the distal direction relative to the housing 12.

The plunger 26 may have a hollow and generally cylindrical or tubular shape. The plunger 26 may include an annular wall 39 with an outer surface 41 and an inner surface 43. The inner surface 43 may define an interior space sized to receive a plunger biasing member 50 therein. It is generally desirable for a thickness of the annular wall 39 to be minimized, to the extent possible without compromising the integrity of the plunger 26, so as to maximize an inner diameter of the plunger 26. This allows a larger diameter plunger biasing member 50 to fit within the interior space of the plunger 26, which, in turn, allows for a more powerful plunger biasing member 50. As described below in more detail, the plunger 26 may be configured to selectively rotate relative to the housing 12 and translate linearly relative to the housing 12 during operation of the drug delivery device 10.

The plunger 26 may be constructed of multiple, interconnected pieces, or alternatively, have a one-piece construction. In the present embodiment, the plunger 26 is constructed of three separate and interconnected structures: a top ring 45 defining a proximal end of the plunger 26; a base 47 defining a distal end of the plunger 26; and a hollow rod 46 positioned between and rigidly connecting the top ring 45 and the base 47. The positions of the top ring 45, the hollow rod 46, and the base 47 may be fixed relative to each other such that these components are immoveable relative to each other. The top ring 45, the hollow rod 46, and the base 47 may each have an annular construction and be centered about the longitudinal axis A. The top ring 45 and the hollow rod 46 may each have a respective central opening extending from end to end of the component to define an axial chamber; whereas, the base 47 may have a central opening extending through the proximal end of the base 47 but which is closed off at the distal end of the base 47. The closed off end of the base 47 may define seat or abutment surface for the plunger biasing member 50. In alternative embodiments, the central opening may extend through the base 47 from end to end. In such alternative embodiments, an inner diameter of the central opening of the base 47 may be smaller than an outer diameter of the plunger biasing member 50 such that the base 47 retains a distal end of the plunger biasing member 50 within the plunger 26. When the drive mechanism 30 is activated, the base 47 may be the portion of the plunger 46 that comes into contact with the stopper 24 to push the stopper 24 in the distal direction.

The top ring 45 may include one or more flanges or projections 48 which extend radially outwardly from a central portion of the top ring 45. Each of the projections 48 may include a distally facing camming surface 49. As described below in more detail, the distally facing camming surface 49 may interact with a counterpart camming surface on a plunger guide 60 in order to release the plunger biasing member 50. In some embodiments, the distally facing camming surface 49 may arranged at angle relative to, or is otherwise non-parallel to, an imaginary plane perpendicular to the longitudinal axis A.

In some embodiments, the top ring 45 and/or the base 47 may be constructed of a different material than the hollow rod 46. In some embodiments, the top ring 45 and/or the base 47 made be constructed of plastic whereas the hollow rod 46 may be constructed of metal. So configured, the plastic material used for the top ring 45 may facilitate the camming action described below by providing sliding friction, the plastic material used for the base 47 may help absorb or attenuate any shock or vibrations associated with base 47 striking the stopper 24. The metal material used for the hollow rod 46 may provide sufficient rigidity to avoid buckling under the biasing force exerted by the plunger biasing member 50. In alternative embodiments, the top ring 45, hollow rod 46, and/or base 47 may be made of the same material, including, for example, metal or plastic. In certain such embodiments, the top ring 45, hollow rod 46, and base 47 may be integrally formed in one piece so as to define single, monolithic structure.

The drug delivery device 10 may further include a guard mechanism for preventing contact with the insertion end 28 of the delivery member 16 when the drug delivery device 10 is not being used to administer an injection. The guard mechanism may include a guard member 32 moveably disposed at the distal end of the housing 12 adjacent to the opening 14. The guard member 32 may have a hollow and generally cylindrical or tubular shape centered about the longitudinal axis A, and may have a proximal end received within the housing 12. The guard member 32 may be configured to move relative to the housing 12 between an extended position wherein a distal end of the guard member 32 extends through the opening 14 in the housing 12 and a retracted position wherein the distal end of the guard member 32 is retracted, fully or partially, into the opening 14 in the housing 12. Additionally or alternatively, the guard member 32 may be configured to move from the retracted position to the extended position. When moving from the extended position to the retracted position, the guard member 32 may translate linearly in the proximal direction; and when moving from the retracted position to the extended position, the guard member 32 may translate linearly in the distal direction. In at least the extended position, the guard member 32 may extend beyond and surround the insertion end 28 of the delivery member 16. In embodiments where the delivery member 16 protrudes from the opening 14 in the housing 12 in the pre-delivery or storage state, moving the guard member 32 from the extended position to the retracted position, e.g., by pressing the distal end of the guard member 32 against the patient's skin at the injection site, may result in the insertion end 28 of the delivery member 16 being inserted into the patient's skin.

For example, the delivery device 10 may utilize inertial design, rather than a spring driven design, to insert the needle into the patient's subcutaneous tissue. As a more specific example, when the patient presses the distal end of the guard member 32 against the patient's skin at the injection site, the delivery device 10 housing 12 may advance toward the injection site. As the patient presses down a predetermined distance or with a predetermined force, the delivery device 10 achieves a quick release to harness the energy stored in the patient's muscles while compressing the needle cover and its spring to a defined release point. The release mechanism is designed such that the resulting needle insertion speed exceeds the patient's reaction speed, and the combination of this speed and the device's mass cause the needle to quickly and fully penetrate the skin to the subcutaneous depth. Compared to known injectors, where the entire primary container is moved forward with respect to the housing, this embodiment prevents relative movement between the drug storage container 20 and the housing and therefore provides a simplified, more robust design.

In some embodiments, the guard member 32 may be rotationally fixed relative to the housing 12. Therefore, although the guard member 32 may able to translate linearly relative to the housing 12, the guard member 32 may be prevented from rotating relative to the housing 12. To achieve this effect, in some embodiments, one or more longitudinal slots 61 may be formed in a wall of the guard member 32 and may be parallel to the longitudinal axis A. Each longitudinal slot 61 may be dimensioned to matingly or snugly receive a projection or pin 63 extending radially inwardly from the front housing 25. Each pin 63 may slidably engage a surface defining a respective one of the longitudinal slots 61 when the guard member 32 translates linearly along the longitudinal axis A relative to the front housing 25. The pin 63, however, abuts against that same surface to prevent rotation of the guard member 32 relative to the front housing 25 if any rotational forces are exerted on the guard member 32. In alternative embodiments, the pin-and-slot arrangement may be reversed, such that the guard member 32 has one or more radially outwardly extending pins and the front housing 25 has one or more slots or other recesses to matingly or snugly receive the one or more pins.

The guard mechanism may further include a guard biasing member 35 and a guard extension 37. The guard extension 37 may be positioned proximal to the guard member 32; and the guard biasing member 35 may be positioned proximal to the guard extension 37. The guard extension 37 may have a hollow and generally cylindrical or tubular shape centered about the longitudinal axis A. Furthermore, the guard extension 37 may be moveable in a linear direction along the longitudinal axis A relative to the housing 12. In the present embodiment, the guard extension 37 is a separate structure from the guard member 32. However, in alternative embodiments, the guard extension 37 and the guard member 32 may be integrally formed in one piece to define a single, monolithic structure. In such alternative embodiments, the proximal end of the guard member 32 may correspond to the guard extension 37.

Similar to the guard member 32, the guard extension 37 may be rotationally fixed relative to the housing 12. Therefore, although the guard extension 37 may able to translate linearly relative to the housing 12, the guard extension 37 may be prevented from rotating relative to the housing 12. To achieve this effect, in some embodiments one or more longitudinal slots 71 may be formed in a wall of the guard extension 37 and may be parallel to the longitudinal axis A. Each longitudinal slot 71 may be dimensioned to matingly or snugly receive a projection or pin (not illustrated) extending radially inwardly from the housing 12, such as, e.g., the rear housing 23 and/or the front housing 25. Each pin may slidably engage a surface defining a respective longitudinal slot 71 when the guard extension 37 translates linearly along the longitudinal axis A relative to the housing 12. The pin, however, abuts against that same surface to prevent rotation of the guard extension 37 relative to the housing 12 if any rotational forces are exerted on the guard extension 37. In alternative embodiments, the pin-and-slot arrangement may be reversed, such that the guard extension 37 has one or more radially outwardly extending pins and the housing 12 has one or more slots or other recesses to matingly or snugly receive the one or more pins.

The guard biasing member 35 may be positioned between and in contact with the guard extension 37 and a releaser member 52. The guard biasing member 35 may be configured to bias or urge the guard extension 37 in the distal direction and bias or urge the releaser member 52 in the proximal direction. The guard biasing member 35 may initially be in an energized (e.g., compressed) state such that it exerts a biasing force on the guard extension 37 and a biasing force on the releaser member 52 in the pre-delivery state. In some embodiments, a distal end of the guard extension 37 is initially in contact with a proximal end of the guard member 32, as seen in FIG. 2. As a consequence, the guard extension 37 transfers a biasing force of the guard biasing member 35 to the guard member 32, such that the guard biasing member 35 biases or urges the guard member 32 toward the extended position. A user may overcome the biasing force by pressing the guard member 32 against the injection site. In doing so, the guard member 32 and the guard extension 37 move jointly in the proximal direction until, for example, the guard member 32 reaches the retracted position. When the injection is complete and the drug delivery device 10 is lifted off of the injection site, the guard biasing member 35 may push the guard extension 37 so that the guard extension 37 and the guard member 32 move jointly in the distal direction. This motion returns the guard member 32 to the extended position, which has the effect of covering the insertion end 28 of the deliver member 16. In some embodiments, the guard biasing member 35 may include a compression spring (e.g., a helical compression spring). Furthermore, in embodiments where the plunger biasing member 50 also includes a compression spring, the guard biasing member 35 may disposed around and/or have a larger diameter than the plunger biasing member 50.

In alternative embodiments, the distal end of the guard extension 37 may initially be spaced in the proximal direction from the proximal end of the guard member 32 by a gap. As a consequence, the guard biasing member 35 may not bias the guard member 32 toward the extended position in the pre-delivery state. When the guard member 32 retracts in the proximal direction and comes into contact with the guard extension 37, only then may the guard biasing member 35 exert the biasing force on the guard member 32 urging it toward the extended position. In such alternative embodiments, a lock ring biasing member 51, described below, may solely be relied upon to bias the guard member 32 toward the extended position in the pre-delivery state.

After drug delivery is complete and the guard member 32 has been re-deployed to the extended position, it may be desirable to lock the guard member 32 in the extended position to prevent subsequent user contact with the insertion end 28 of the delivery member 16 and/or to prevent re-use of the drug delivery device 10. Pursuant to these ends, some embodiments of the drug delivery device 10 may include a lock ring 40 configured to selectively rotate, depending on the axial position of the guard member 32, in order to lock the guard member 32 in the extended position once the guard member 32 has moved from the retracted position to the extended position. In the present embodiment, the lock ring 40 is centered and rotates about the longitudinal axis A. As illustrated in FIG. 2, a proximal end of the lock ring 40 may be in contact with the container holder 31 and the distal end of the lock ring 40 may be disposed at least partially within the guard member 32. The lock ring biasing member 51 may be positioned in the axial direction between a distally facing surface of the lock ring 40 and a proximally facing surface of the guard member 32. The lock ring biasing member 51 may initially be in a compressed or energized state such that it biases the lock ring 40 and the guard member 32 away from each other. As such, the lock ring biasing member 51 may exert a biasing force urging the guard member 32 toward the extended position, as well as exert a biasing force urging the proximal end of the lock ring 40 against the container holder 31. In some embodiments, the lock ring biasing member 51 may include a compression spring (e.g., a helical compression spring).

Rotation of the lock ring 40 may be achieved by a camming arrangement between the lock ring 40 and the container holder 31. In some embodiments, the proximal end of the lock ring 40 may include one or more camming surfaces 53 configured to slidably engage one or more corresponding camming surfaces 55 included on an inner annular wall 57 of the front housing 25. The inner annular wall 57 of the front housing 25 may be centered about the longitudinal axis A and may be cantilevered radially inwardly from an outer annular wall 59 of the front housing 25 such that an annular gap exists between the inner annular wall 57 and the outer annular wall 59 of the front housing 25. This configuration may allow for the guard member 32 to slide into the annular gap between the inner and outer walls 57 and 59 during retraction. In some embodiments, the camming surfaces 53 of the lock ring 40 may have a generally saw tooth appearance when viewed in the radial direction from the longitudinal axis A. Furthermore, the camming surfaces 53 may be disposed around the longitudinal axis A such that each camming surface 53 is located at different angular position around the longitudinal axis A.

Similarly, the camming surfaces 55 on the container holder 31 may have a generally saw tooth appearance when viewed in the radial direction from the longitudinal axis A. Furthermore, the camming surfaces 55 may be disposed around the longitudinal axis A such that each camming surface 55 is located at different angular position around the longitudinal axis A.

When pressed against one another, the camming surfaces 53 and 55 may convert linear motion into a combination of rotational motion and linear motion. More particularly, when the lock ring 40 moves in the proximal direction along the longitudinal axis A, each of the camming surfaces 53 may slide against a respective one of the camming surfaces 55. This interaction may convert the proximal linear movement of the lock ring 40 into a combination of rotational movement of the lock ring 40 about the longitudinal axis A and proximal linear movement of the lock ring 40 along the longitudinal axis A. Throughout movement of the lock ring 40, the inner annular wall 57 of the front housing 25 remains stationary relative to a remainder of the front housing 25. So configured, the inner annular wall 57 of the front housing 25 functions as a cam and the lock ring 40 as a cam follower.

The biasing force of the guard biasing member 35 may continuously press the camming surfaces 53 of the lock ring 40 against the camming surfaces 55 of the inner annular wall 57. As a consequence, the lock ring 40 is continuously urged to rotate about the longitudinal axis A. However, the lock ring 40 may not rotate depending on the relative positions of various cooperating abutment structures included on the exterior of the lock ring 40 and the interior of the guard member 32. Depending on the axial position of the guard member 32, these cooperating abutment structures may come into and/or out of engagement with each other to allow the lock ring 40 to rotate. In some embodiments, the lock ring 40 may rotate into a final rotational position upon the guard member 32 moving from the retracted position to the extended position. In the final rotation position, a distally facing surface of one or more of the abutment structures included on the lock ring 40 may be rotationally aligned with and arranged in opposition to a proximally facing surface of one or more of the counterpart abutment structures included on the guard member 32. As a consequence, any subsequent movement of the guard member 32 in the proximal direction may be prevented by the distally surface(s) of the abutment structure(s) included on the lock ring 40 engaging the proximally facing surface(s) of the abutment structure(s) included on the guard member 32.

The drug delivery device 10 may further include a drive mechanism 30 disposed partially or entirely within the housing 12. Generally, the drive mechanism 30 may be configured to store energy and, upon or in response to activation of the drive mechanism 30 by the user, release or output that energy to drive the plunger 26 to expel the drug 22 from the drug storage container 20 through the delivery member 16 into the patient. In the present embodiment, the drive mechanism 30 is configured to store mechanical potential energy; however, alternative embodiments of the drive mechanism 30 may be configured differently, for example, with the drive mechanism 30 storing electrical or chemical potential energy. Generally, upon activation of the drive mechanism 30, the drive mechanism 30 may convert the potential energy into kinetic energy for moving the plunger 26.

In the present embodiment, the drive mechanism 30 includes the plunger biasing member 50, a plunger biasing member seat 38, the releaser member 52, and a plunger guide 60. The plunger biasing member 50 may include a compression spring (e.g., a helical compression spring) which is initially retained in an energized state. In the energized state, the plunger biasing member 50 may be compressed such that its axial length is shorter than it would be in a natural or de-energized state. When released, the plunger biasing member 50 may try to expand to its natural axial length, and as a consequence, exert a biasing force pushing the plunger 26 in the distal direction.

The plunger biasing member 50 may be disposed at least partially within the plunger 26, and may have a distal end abutting against a proximally facing inner surface of the plunger 26 and/or may be fixedly attached to an inner surface of the plunger 26. So that the plunger biasing member 50 may be received within the plunger 26, an outer diameter or other dimension of the plunger biasing member 50 may be equal to or less than an inner diameter of the top ring 45 and/or equal to or less than an inner diameter of the hollow rod 46. In some embodiments, the distal end of the plunger biasing member 50 may abut against a proximally facing inner surface of the base 47 of the plunger 26. Furthermore, a proximal end of the plunger biasing member 50 may abut against a distally facing surface of the plunger biasing member seat 38. The plunger biasing member seat 38 may be fixedly attached to the rear housing 27 such that the plunger biasing member seat 38 provides a stationary surface for the plunger biasing member 50 to push off of. So configured, the plunger biasing member 50, when released from the energized state, may expand in length with distal end of the plunger biasing member 50 moving in the distal direction away from the stationary proximal end of the plunger biasing member 50. This motion may push the plunger 26 is the distal direction, which, in turn, may push the stopper 24 in the distal direction to expel the drug 22 from the drug storage container 20 into the delivery member 16 and thereafter into the patient.

The plunger guide 60 may be fixedly attached to the rear housing 27 such that the plunger guide 60 is immovable relative to the rear housing 27. The plunger guide 60 may have a hollow and generally cylindrical or tubular shape, and may be centered about the longitudinal axis A. An outer diameter or other outer dimension of a proximal end of the plunger guide 60 may be larger than an outer diameter or other outer dimension of a distal end of the plunger guide 60. At least a portion of the distal end of the plunger guide 60 may be positioned radially between the plunger 26 and the releaser member 52. As such, the plunger 26 may be disposed at least partially within the distal end of the plunger guide 60, and the distal end of the plunger guide 60 may be disposed at least partially within the releaser member 52, as illustrated in FIG. 2.

Example grippers or needle shield removers 100 are shown in FIGS. 4-22. In each of the example forms, the removers 100 include a body 102 that has a tubular configuration. The body 102 is formed from a rectangular sheet 104 (FIG. 19) of material having first and second longitudinal side edges 106, 108 and end edges 110 extending between the side edges 106, 108. The tubular configuration of the body 102 is created by bringing the side edges 106, 108 together and securing the edge 106, 108 together with a closure 112. As shown, the closure 112 includes a plurality of teeth 114 that extend outwardly from the first side edge 106 and a plurality of grooves 116 that extend inwardly from the second side edge 108, where the tabs 114 are configured to be inserted into the grooves 116 to thereby hold the sheet 104 in the tubular configuration of the remover 100.

Figure 5:
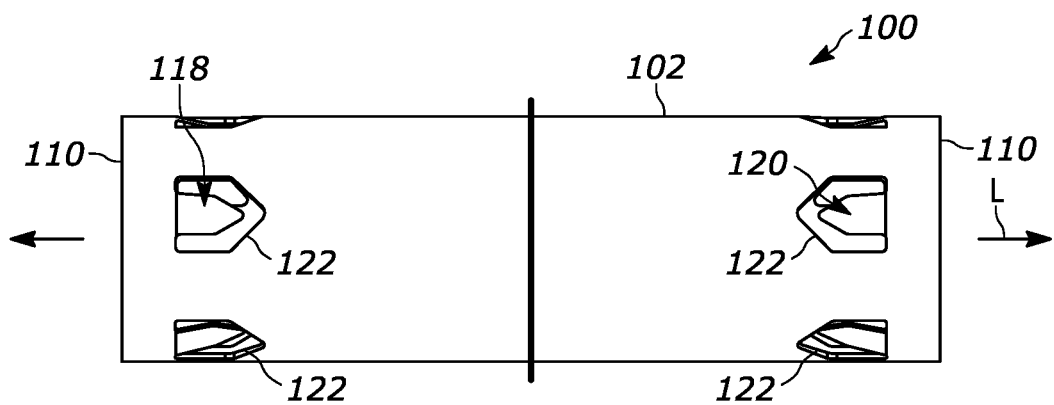
FIG. 5 is a front elevational view of the needle shield remover of FIG. 4.
Figure 6:
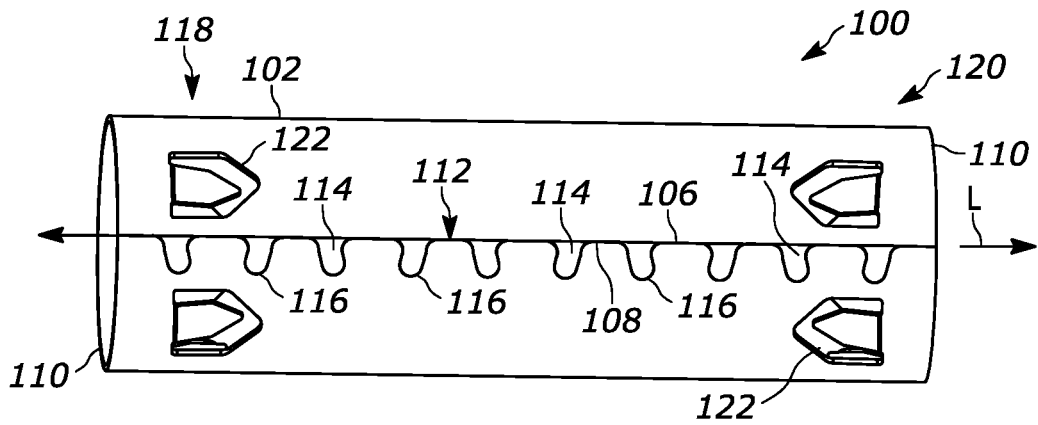
FIG. 6 is a perspective view of a second example needle shield remover showing a closure holding the needle shield remover in a tubular configuration according to various embodiments of the present disclosure.

As shown in FIGS. 5 and 6, the removers 100 include a first array of barbs 118 extending around a circumference of the body 102 adjacent to a first one of the end edges 110 and a second array of barbs 120 extending around a circumference of the body 102 adjacent to a second one of the end edges 110. The first and second arrays of barbs 118, 120 are configured to grip the sterile barrier 21 disposed on the delivery member 16 of the syringe 20 and the removable cap 19, respectively, such that removal of the cap 19 from the device 10 also causes the sterile barrier 21 to be removed from the delivery member 16. The first and second arrays of barbs 118, 120 can each be disposed in a plane generally perpendicular to a longitudinal axis L of the body 102. In one form, the removers 100 can be symmetrical about a central plane extending perpendicular to the longitudinal axis L through a midpoint of the body 102, which advantageously allows the remover 100 to be installed within the device 10 in either orientation and the barbs 118, 120 can effectively grip the cap 19 and sterile barrier 21, respectively. By one approach, the barbs 118, 120 can be formed by creating an opening 122 within the sheet 104 of material that forms the shape of the individual barbs 118, 120. Thereafter, the barbs 118, 120 can be bent radially with respect to the longitudinal axis L so that the barbs 118, 120 grip structure disposed adjacent to the remover 100. As shown, both arrays of barbs 118, 120 can be bent to extend radially inwardly into the body 102 of the remover 100, which advantageously prevents the barbs 118, 120 from entangling the removers 100 together or to other structures. This, combined with the symmetrical configuration, allows for efficient and effective assembly of the remover 100 to the device 10.

Figure 7:
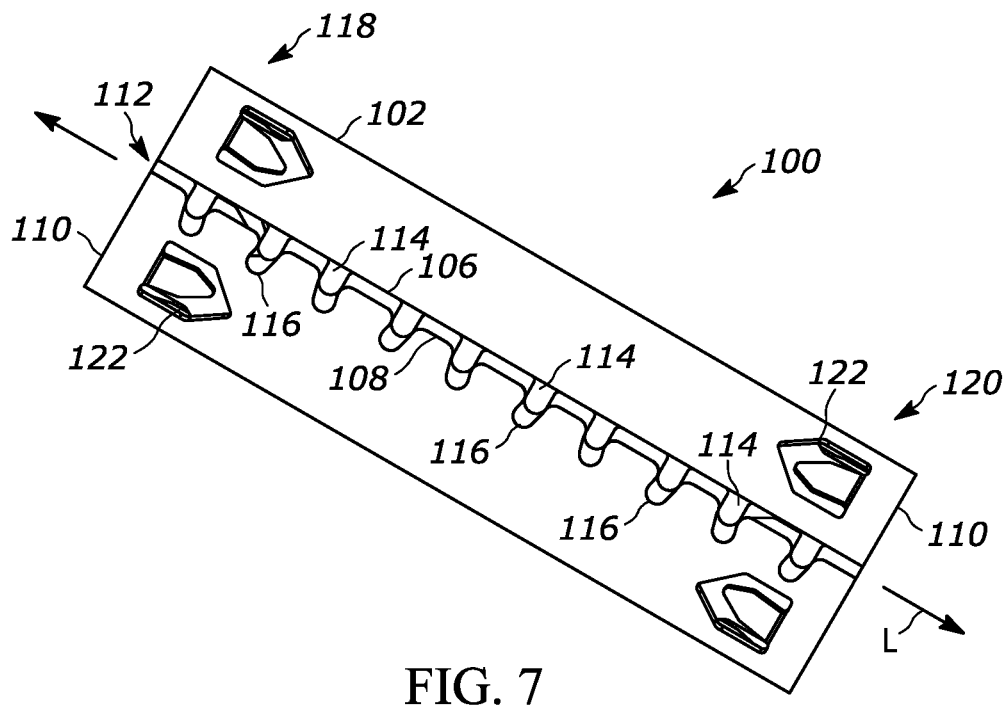
FIG. 7 is a perspective view of the needle shield remover of FIG. 6 showing the closure in an open configuration.

Details of one example configuration for the teeth 114 and grooves 116 are shown in FIGS. 6 and 7. As shown, in this configuration, the teeth 114 extend perpendicularly away from the first side edge 106, while the grooves 116 extend inwardly away from the second side edge 108 at an angle with respect thereto. With this configuration, the teeth 114 are bent and flexed as they are forced into the angled configuration of the grooves 116. This bending action effectively retains the teeth 114 within the grooves 116 to thereby hold the body 102 in the tubular configuration without the use of welding or other methods of securing the edges 106, 108 together. In some examples, the grooves 116 can extend at an angle with respect to the second side edge 108 between 5 degrees and 20 degrees, between 10 degrees and 20 degrees, or between 15 degrees and 20 degrees. In the illustrated form, the grooves 116 have a staggered configuration, such that the grooves 116 sequentially extend above and below planes extending perpendicularly through the longitudinal axis L of the body 102 or horizontal lines extending between the first and second side edges 106, 108. As shown, the teeth 118 can have a tab-like configuration with generally parallel side edges 124 and a rounded end 126 and the grooves 120 can have an opening with a complementary configuration with generally parallel side edges 128 and rounded end 130 sized to frictionally receive one of the teeth 118 therein. Other configurations, such as all the grooves angled in the same direction, a repeating pattern of two or three grooves extending in the same direction, or random directions.

Figure 8:
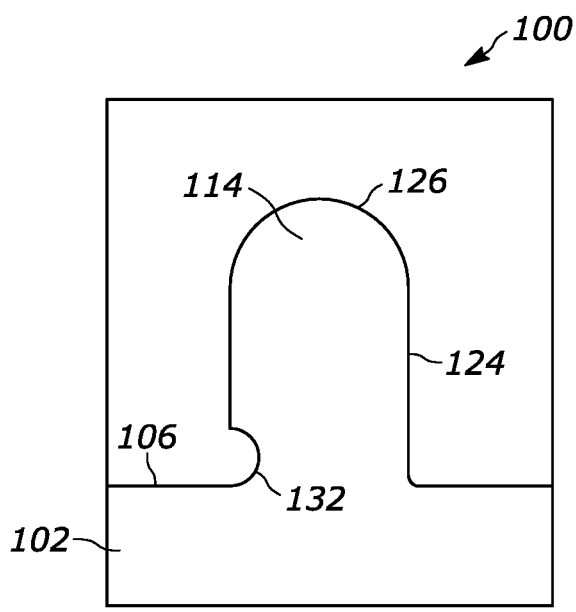
FIG. 8 is a sectional view of a first example tooth configuration for the closure of FIG. 6.
Figure 9:
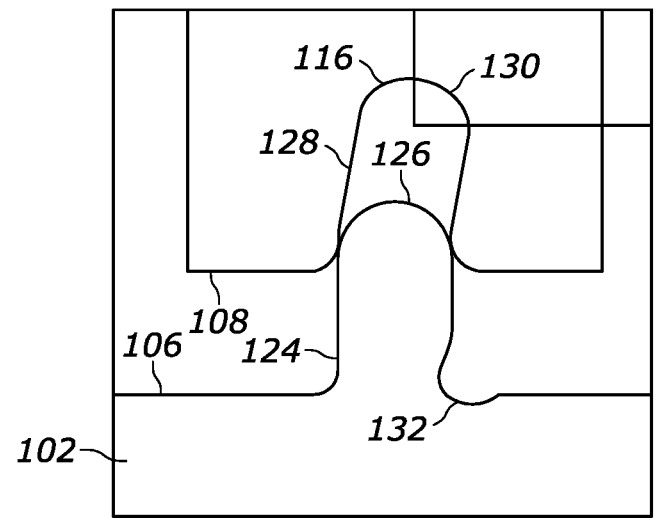
FIG. 9 is a sectional view of a second example tooth configuration for the closure of FIG. 6 along with a groove of the closure.

If desired, as shown in FIGS. 8 and 9, each of the teeth 118 can include an associated cut-out portion 132 on a side of the individual tooth 118 facing in the direction of the angle of the associated groove 120 configured to relieve stress due to the bending and flexing that results from the tooth 118 being inserted into the angled groove 120. In a first form, the cut-out portion 132 can be disposed in the side edge 124 of the tooth 118 adjacent to the second side edge 108 of the sheet 104, such that the cut-out portion 132 extends into the tooth 118. In a second form, the cut-out portion 132 can be disposed in a corner between the side edge 124 of the tooth 118 and the second side edge 108 of the sheet 104, such that the cut-out portions 132 extends inwardly into the tooth 118 and sheet 104. The cut-out portions 132 can have a curved shape, formed by a circular or oval punch, for example.

Figure 10:
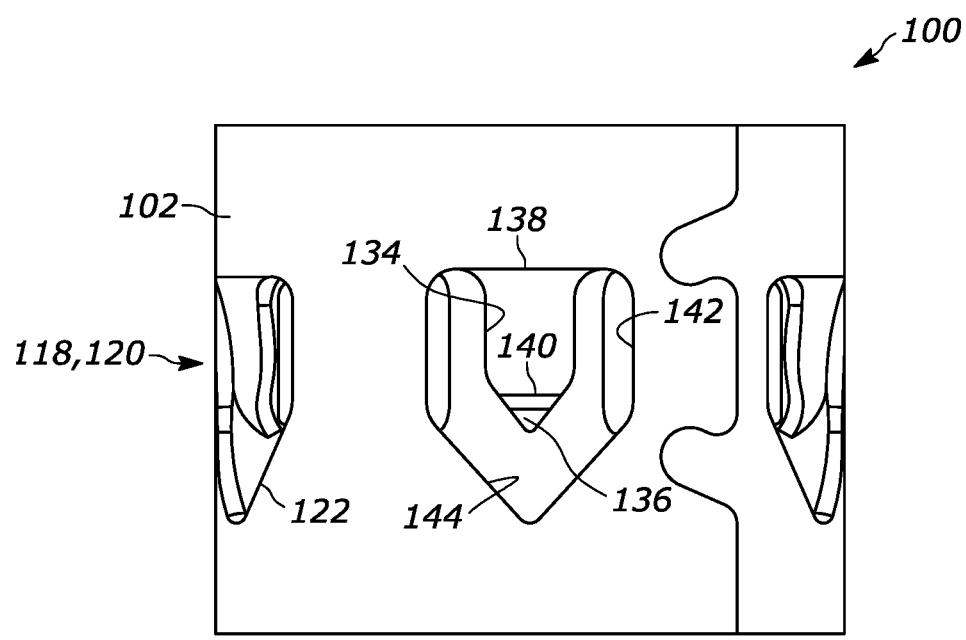
FIG. 10 is a sectional view of a first example barb configuration for the needle shield remover of FIG. 6.
Figure 11:
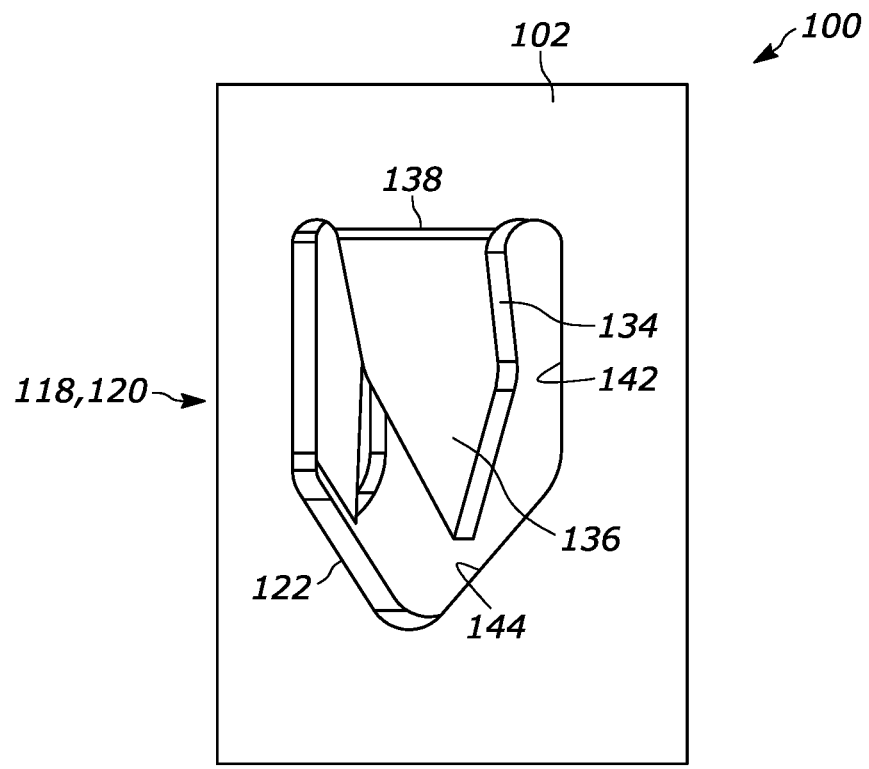
FIG. 11 is a sectional view of a second example barb configuration for the needle shield remover of FIG. 6.
Figure 12:
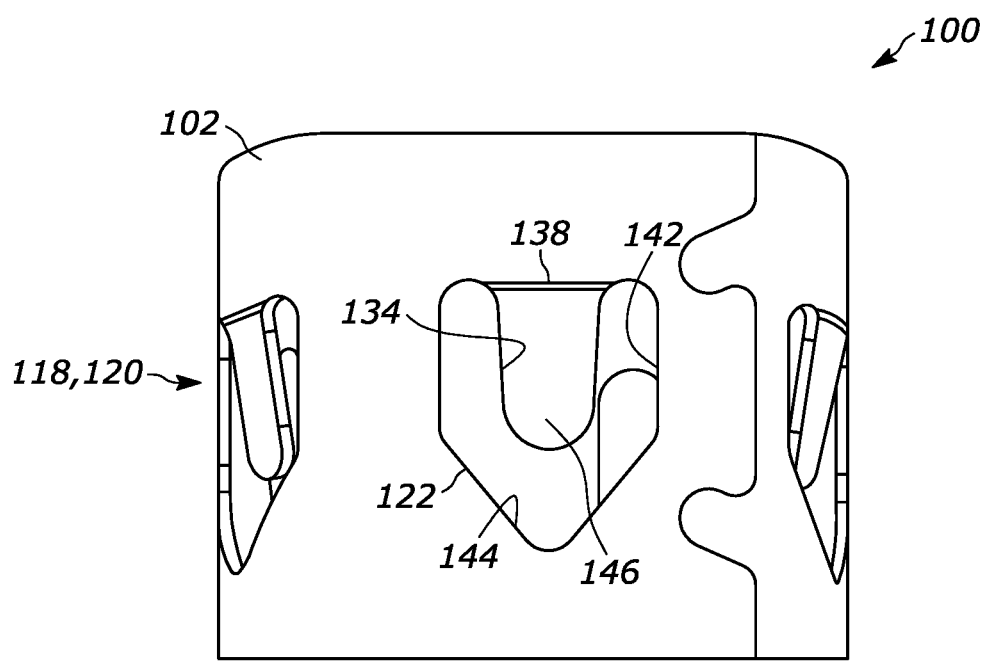
FIG. 12 is a sectional view of a third example barb configuration for the needle shield remover of FIG. 6.
Figure 13:
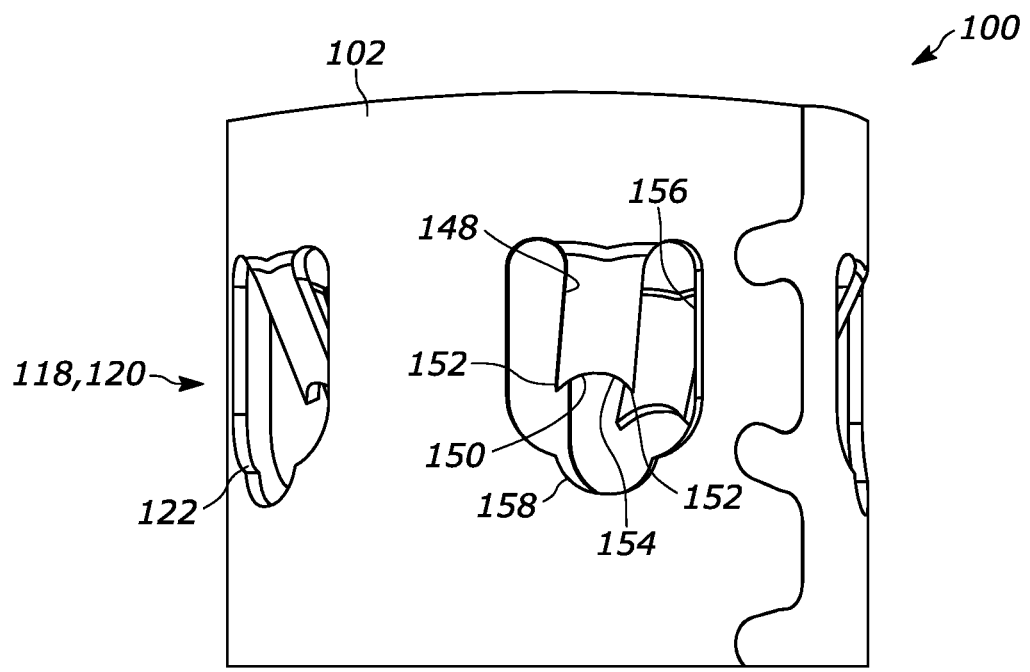
FIG. 13 is a sectional view of a fourth example barb configuration for the needle shield remover of FIG. 6.
Figure 14:
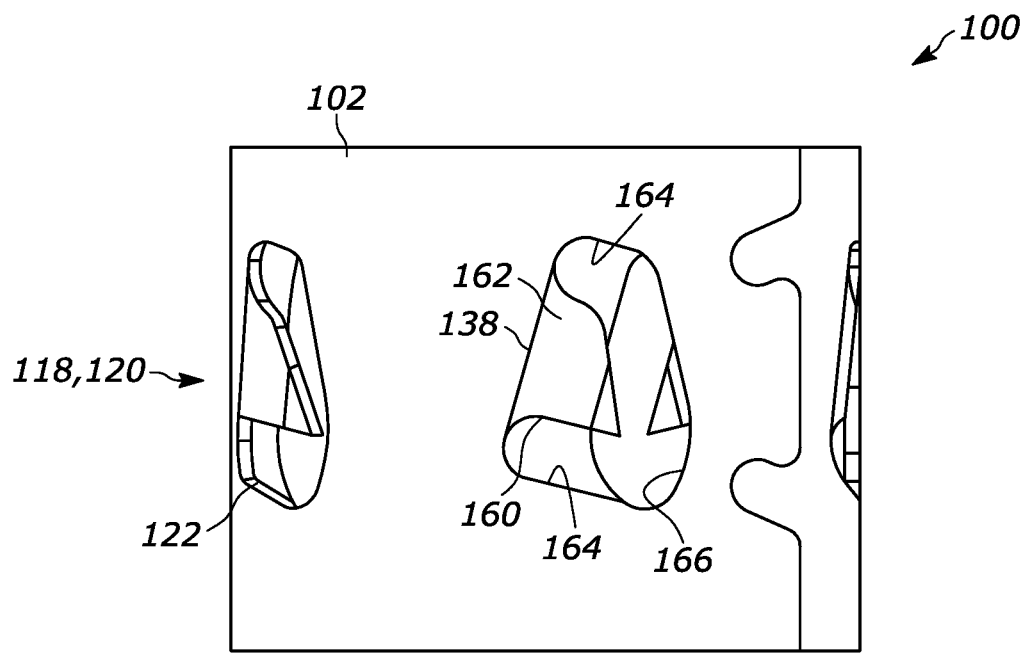
FIG. 14 is a sectional view of a fifth example barb configuration for the needle shield remover of FIG. 6.
Figure 15:
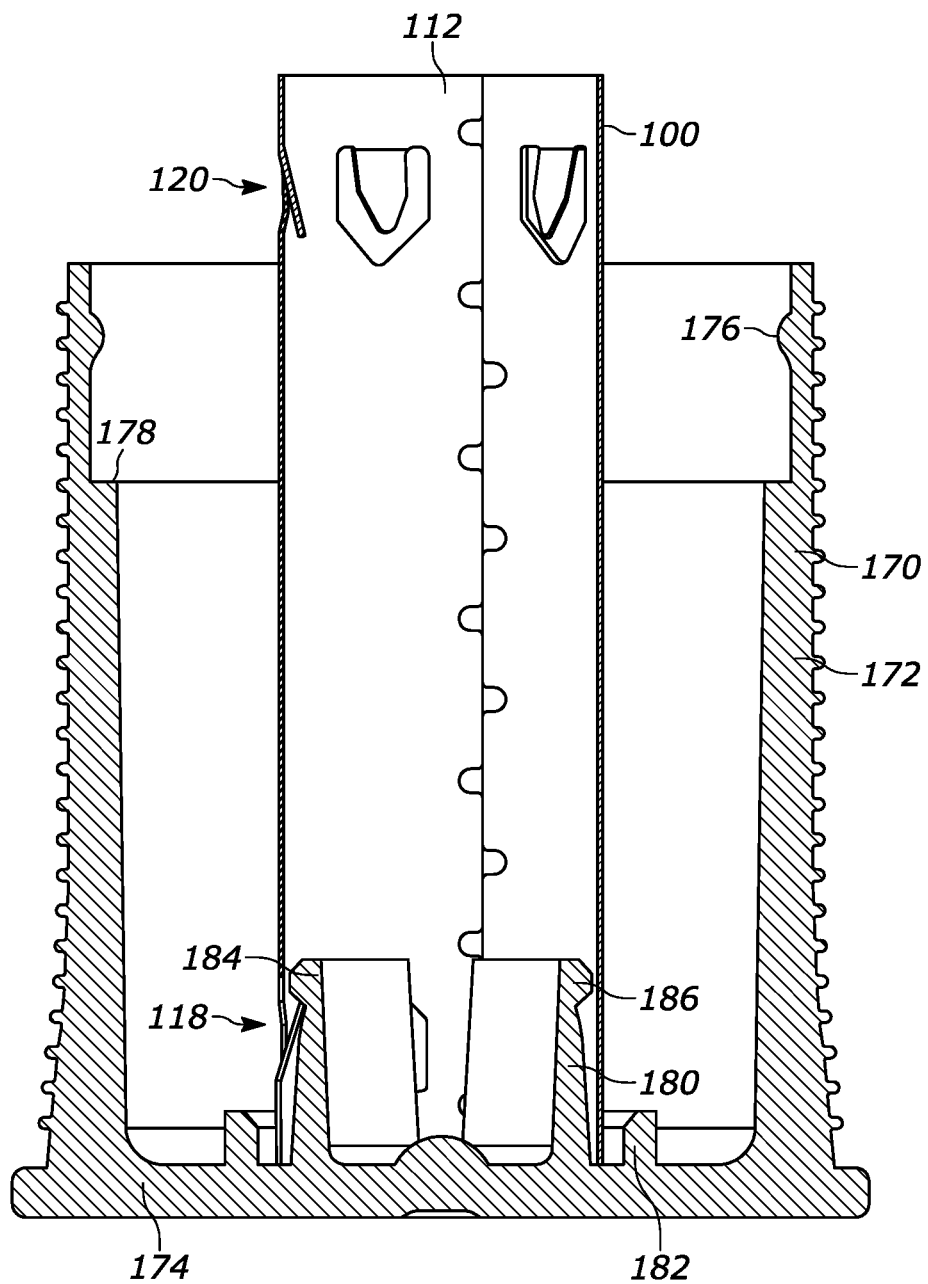
FIG. 15 is a cross-sectional view of the needle shield remover of FIG. 6 mounted to a removable cap for a drug delivery device according to various embodiments of the present disclosure.
Figure 16:
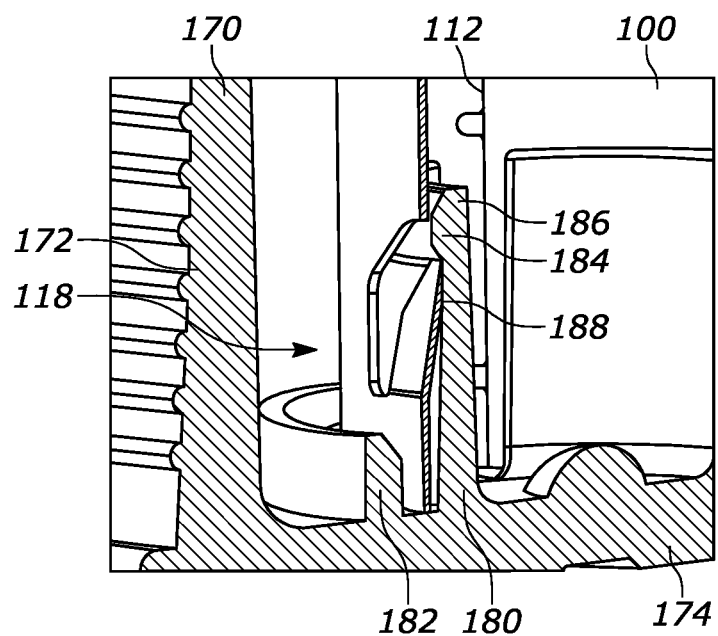
FIG. 16 is a sectional view of the needle shield remover and removable cap of FIG. 15.

Example configurations for the barbs 118, 120 are shown in FIGS. 10-14. In a first form shown in FIGS. 10 and 11, the barbs 118, 120 have a pointed configuration with side edges 134 extending to a pointed tip 136. The barbs 118, 120 of this form can be bent radially inwardly into an interior of the body 102 along a bottom edge 138 of the barb 118, 120, where the barb 118, 120 joins the rest of the body 102 (FIG. 10) and/or along an intermediate edge of the barb 118, 120 extending between ends of the side edges 134 adjacent to the pointed tip 136 to thereby angle the tip 136 inwardly (FIG. 11). The opening 122 can have a complementary configuration extending around and defining the barb 118, 120 with side portions 142 extending along the side edges 134 of the barb 118, 120 and a pointed end portion 144 extending around the pointed tip 136 of the barb 118, 120. In a second form shown in FIG. 12, rather than a pointed tip 136 as shown in FIGS. 10 and 11, the barb 118, 120 can have a rounded tip 146, with the barb 118, 120 bent inwardly along the bottom edge 138. In a third form, shown in FIG. 13, the barb 118, 120 can have a pronged configuration with side edges 148 extending to a pronged end 150 that includes two laterally spaced pointed tips 152. In the illustrated form, the pointed tips 152 are defined by the side edges 148 of the barb 118, 120 and a concavely curved end edge 154, but other configurations for the end edge 154 can be utilized, such as angled portions and the like. Alternatively, the pointed tips 152 can extend outwardly from the end edge 154. The barb 118, 120 can be bent inwardly along a bottom edge 155 thereof. The opening 122 of this form can have a complementary configuration extending around and defining the barb 118, 120 with side portions 156 extending along the side edges 148 of the barb 118, 120 and a circular end portion 158 defining the curved end edge 154 of the barb 118, 120. In other versions, the barb 118, 120 can be configured with a with an end having three or more pointed tips. In each of the first through third forms, the barbs 118, 120 extend longitudinally along the axis L and are oriented inwardly toward a longitudinal center of the body 102. In a fourth form, shown in FIG. 14, the barbs 118, 120 extend at an angle with respect to the longitudinal axis L of the body 102 and have a pointed configuration with side edges 160 extending to a pointed tip 162. Rather than a symmetrical tip as shown in the earlier forms, the pointed tip 162 of the barb 118, 120 of this form is offset in a direction of a midpoint of the body 102 such that the tip 162 is oriented toward the midpoint while the barb 118, 120 extends at an angle with respect thereto. Due to this configuration, the opening 122 of this form includes side portions 164 that have differing lengths, i.e., a smaller top portion and larger bottom portion, and an end portion 166 that extends at an angle between ends of the side portions 164.

An example removable cap 170, suitable for use as the cap 19 described above, is shown in FIGS. 15 and 16. As shown, the cap 170 includes an upstanding annular sidewall 172 and an end wall 174. The sidewall 172 can include an inwardly protruding lip 176 and ledge 178 to engage the housing 12 of the device 10. The cap 170 further includes concentrically disposed annular walls 180, 182 extending upwardly from the end wall 174. The inner wall 180 includes an outwardly protruding lip 184 at a distal end 186 thereof and, if desired, can include an inwardly tapered portion 188 adjacent to the lip 184 to provide access to an underside of the lip 184. The inner wall 180 is sized to have a radius that fits within the cylindrical body 102 of the remover 100 so that the body 102 can be mounted therearound. Advantageously, the lip 184 can protrude radially outwardly a distance sufficient for the barbs 120 of the remover 100 to project thereunder to thereby mount the remover 100 to the cap 170. The outer wall 182 is spaced radially outwardly from the inner wall 180 a sufficient distance to receive the body 102 therebetween. With this configuration, the outer wall 182 can brace an outer surface of the end of the body 102 and prevent the end of the body 102 from deflecting radially outwardly, such as may happen if a tensile force is applied to the remover 100 by pulling the cap 170 away from the device 10. While the depicted cap 170 includes both the inner wall 180 and the outer wall 182, an alternative variation only includes the inner wall 180 and no outer wall 182.

Figure 17:
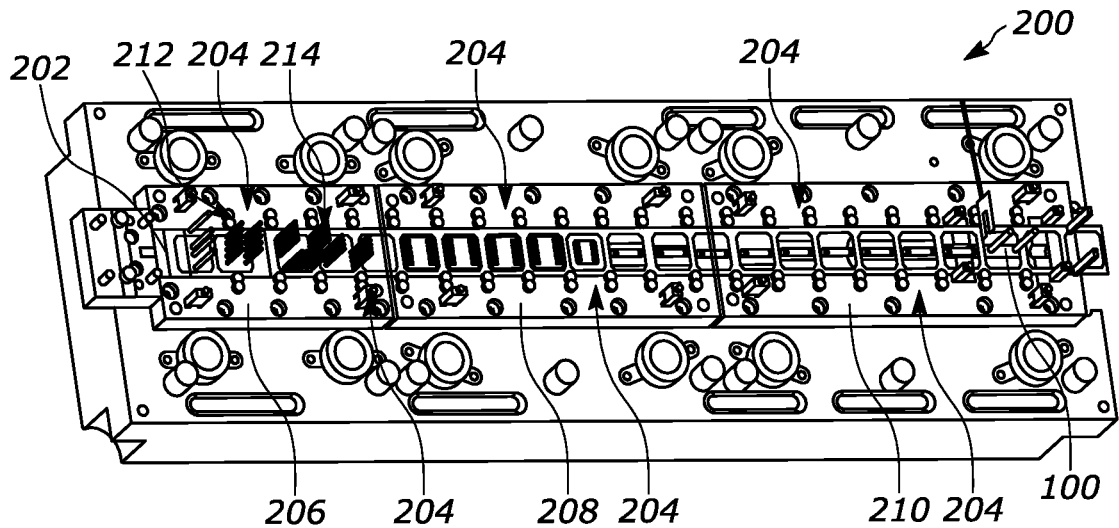
FIG. 17 is an exploded perspective view of stamping tool for forming the needle shield remover of FIG. 6.
Figure 18:
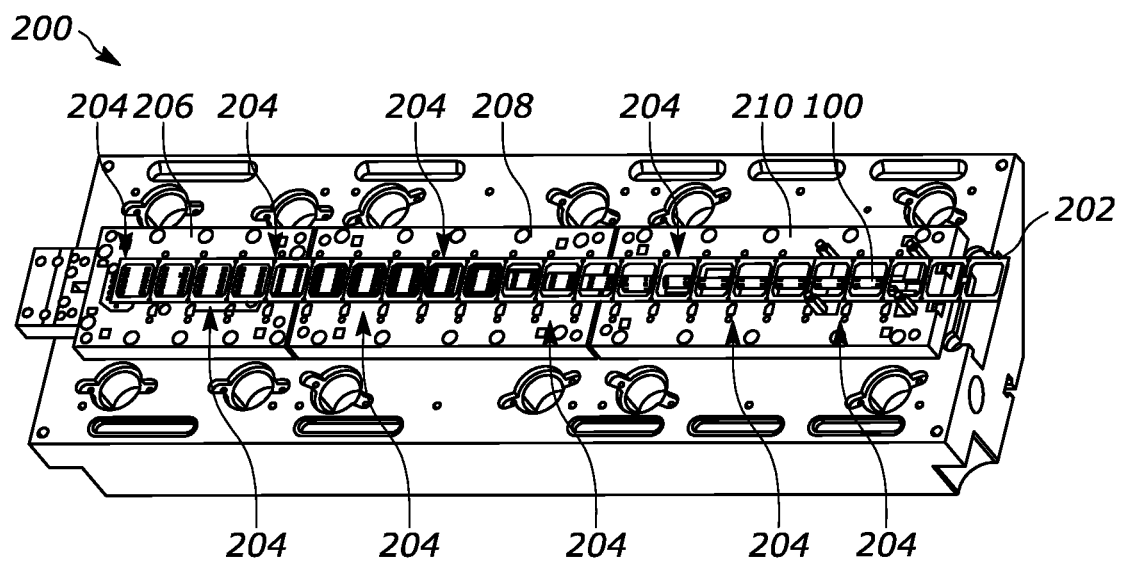
FIG. 18 is a perspective view of the stamping tool of FIG. 17.
Figure 19:
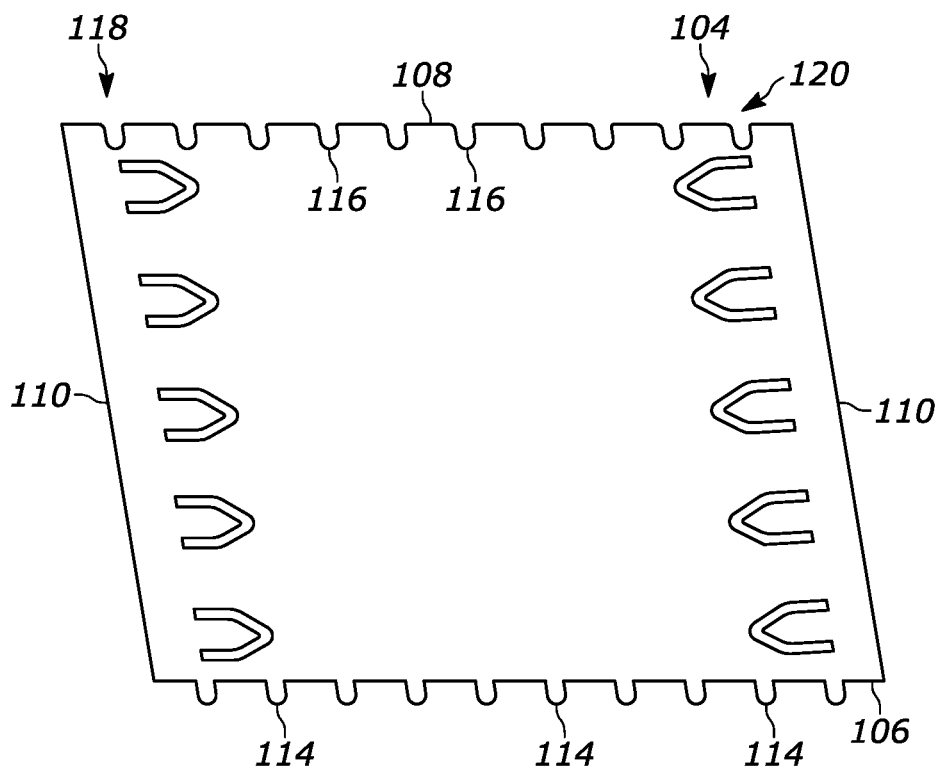
FIG. 19 is a perspective view of a sheet of material having first and second arrays of barbs and a closure formed therein to create the needle shield remover of FIG. 6.
Figure 20:
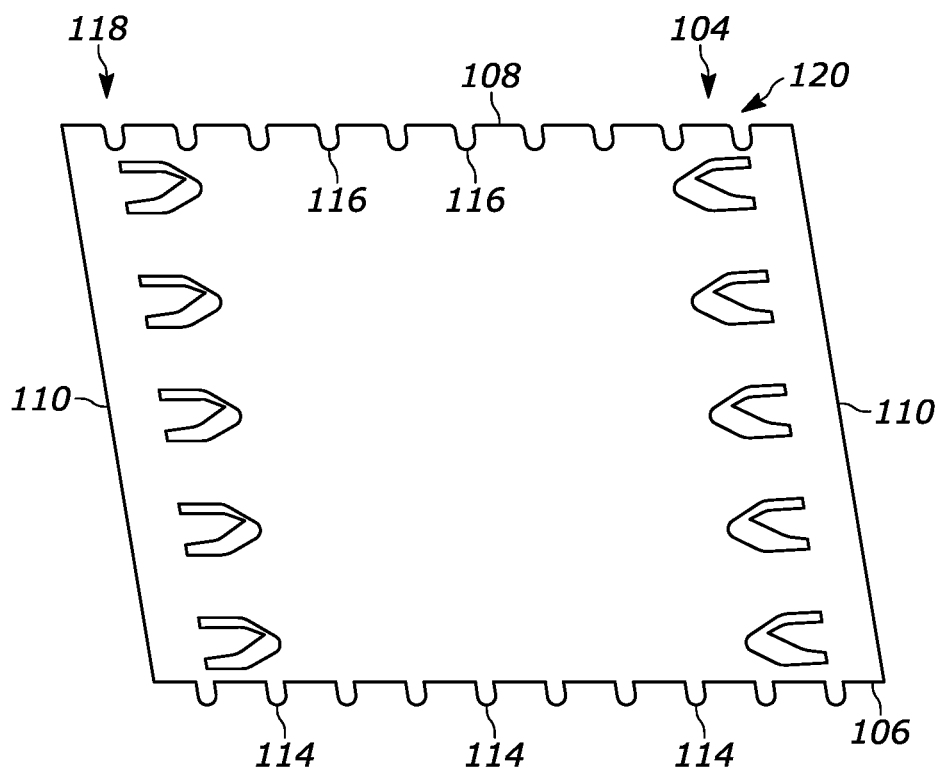
FIG. 20 is a perspective view of the sheet of material of FIG. 19 with the first and second arrays of barbs bent upwardly.
Figure 21:
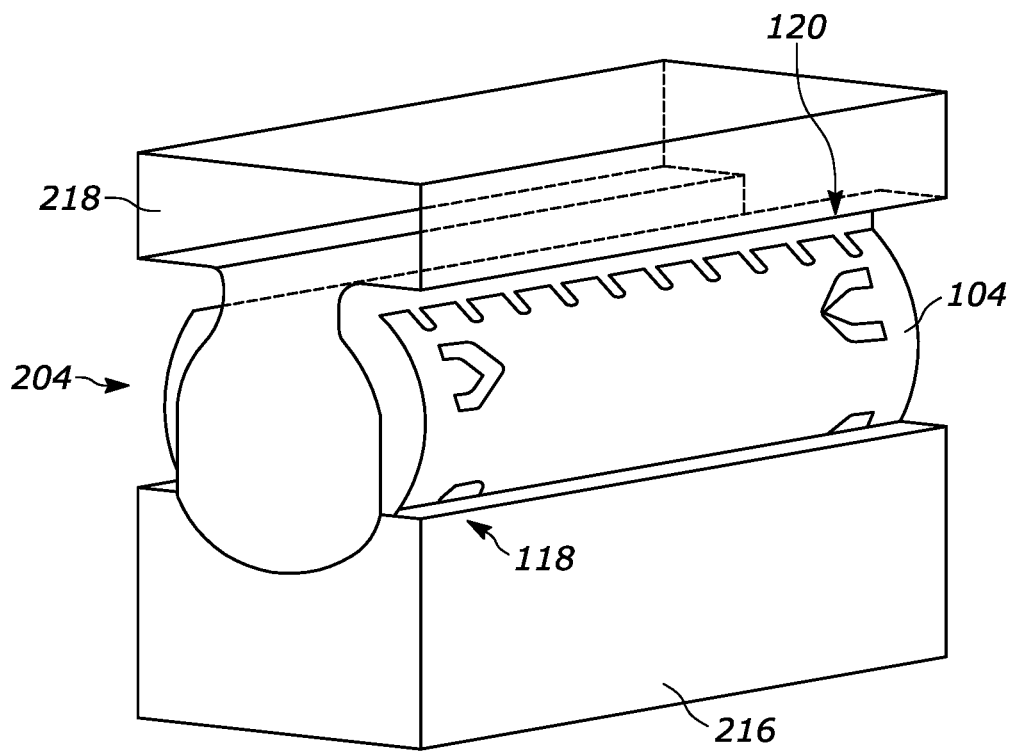
FIG. 21 is a perspective view of a tool station configured to bend the sheet of material of FIG. 19 into a tubular shape.
Figure 22:
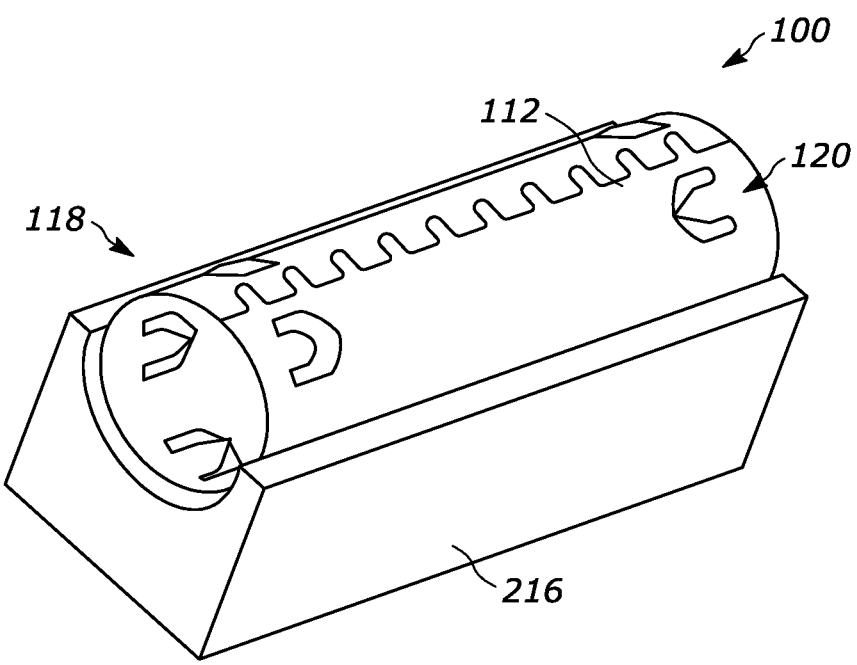
FIG. 22 is a perspective view of a bottom form of the tool station of FIG. 21 showing the sheet of material formed into the needle shield remover of FIG. 6.

The removers 100 described above can advantageously be mass produced in a high-speed stamping tool 200 as shown in FIGS. 17 and 18. In operation, a strip 202 of metal is fed into the tool 200 and the tool 200 performs sequential operations to form features on individual portions of the strip 202 to transform the strip 202 into the sheets 104 and subsequently form the body 102 by engaging the teeth 114 and grooves 116 of the closure 112. Pursuant to this, the tool 200 can include a plurality of stations 204 and the strip 202 can be fed through the tool 200 such that the stations 204 sequentially perform operations on the strip 202 to ultimately form the remover 100. The stations 204 of the tool 200 can be provided on three blocks 206, 208, 210 as shown. The stations 204 in the first block 206 utilize punches 212 to make guide holes in the strip 202 to pattern the edges 106, 108, 110 of the sheet 104, the teeth 114, the grooves 116, and the first and second arrays of barbs 118, 120 and the associated openings 122. Subsequent stations 204 in the first block 206 and stations 204 in the second block 208 then cut the strip 202 with punches 214 to form the sheet 104 (FIG. 19) including the teeth 114, grooves 116, and barbs 118, 120 thereof. The guide holes formed in the first block 206 allow the sheet 104 to be formed without substantially distorting the thin metal of the strip 202. The stations 204 in the second block 208 can further bend the barbs 118, 120 inwardly a desired angle along the bottom and/or intermediate edge, as discussed above as shown in FIG. 20, and starting the bending process to sequentially form a cylindrical shape from the sheet 104. The stations 204 in the third block 210 then fully form the tubular shape of the body 102 by forcing the teeth 114 into the grooves 116 to interlock the edges 106, 108 with high forces. As shown in FIGS. 21 and 22, the stations 204 configured to bend the body 102 into the cylindrical shape include a lower concave form 216 and an upper convex form 218 that are configured to be pressed together to thereby bend the sheet 104.

The cold formation process and forces imparted to the sheet 104 to interlock the teeth 114 and grooves 116 can slightly elongate the body 102. For example, the body 102 can be extended by about 0.15 during the formation process. In the illustrated form, the tool 200 is about 3 feet long and 1.25 feet wide. The tool 200 is configured to receive a feed of a 3 inch wide and 0.078 inch thick metal strip 202. Every time the tool 200 closes and opens, which corresponds to one stroke, the strip 202 can be moved forward about 1 inch to align the portion of the strip 202 with the next station 204 in the tool 200. The tool 200 as shown includes twenty two total stations 204. It will be understood, however, that the tool 204 can have any desired layout and configuration for creating removers 100 having the features described herein.

It will be appreciated that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. The same reference numbers may be used to describe like or similar parts. Further, while several examples have been disclosed herein, any features from any examples may be combined with or replaced by other features from other examples. Moreover, while several examples have been disclosed herein, changes may be made to the disclosed examples within departing from the scope of the claims.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF), UDENYCA® (pegfilgrastim-cbqv), Ziextenzo® (LA-EP2006; pegfilgrastim-bmez), or FULPHILA (pegfilgrastim-bmez).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 145c7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like;Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa) Erythropoietin [30-asparagine, 32-threonine, 87-valine, 88-asparagine, 90-threonine], Darbepoetin alfa, novel erythropoiesis stimulating protein (NESP); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Kanjinti™ (trastuzumab-anns) anti-HER2 monoclonal antibody, biosimilar to Herceptin®, or another product containing trastuzumab for the treatment of breast or gastric cancers; Humatrope® (somatropin, Human Growth Hormone); Humira® (adalimumab); Vectibix® (panitumumab), Xgeva® (denosumab), Prolia® (denosumab), Immunoglobulin G2 Human Monoclonal Antibody to RANK Ligand, Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Mvasi™ (bevacizumab-awwb); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 145c7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-198); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCG3 mAb (MDX-1307); anti-mesothelin dsFv-PE38 conjugate (CAT-5001); anti-PD1mAb (MDX-1106 (ONO-4538)); anti-PDGFRa antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, BPS 804 (Novartis), Evenity™ (romosozumab-aqqg), another product containing romosozumab for treatment of postmenopausal osteoporosis and/or fracture healing and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoV-EXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. In some embodiments, the drug delivery device may contain or be used with Aimovig® (erenumab-aooe), anti-human CGRP-R (calcitonin gene-related peptide type 1 receptor) or another product containing erenumab for the treatment of migraine headaches. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BiTE®) antibodies such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure. In some embodiments, the drug delivery device may contain or be used with Avsola™ (infliximab-axxq), anti-TNF α monoclonal antibody, biosimilar to Remicade® (infliximab) (Janssen Biotech, Inc.) or another product containing infliximab for the treatment of autoimmune diseases. In some embodiments, the drug delivery device may contain or be used with Kyprolis® (carfilzomib), (2S)-N-((S)-1-((S)-4-methyl-1-((R)-2-methyloxiran-2-yl)-1-oxopentan-2-ylcarbamoyl)-2-phenylethyl)-2-((S)-2-(2-morpholinoacetamido)-4-phenylbutanamido)-4-methylpentanamide, or another product containing carfilzomib for the treatment of multiple myeloma. In some embodiments, the drug delivery device may contain or be used with Otezla® (apremilast), N-[2-[(1S)-1-(3-ethoxy-4-methoxyphenyl)-2-(methylsulfonyl)ethyl]-2,3-dihydro-1,3-dioxo-1H-isoindol-4-yl]acetamide, or another product containing apremilast for the treatment of various inflammatory diseases. In some embodiments, the drug delivery device may contain or be used with Parsabiv™ (etelcalcetide HCl, KAI-4169) or another product containing etelcalcetide HCl for the treatment of secondary hyperparathyroidism (sHPT) such as in patients with chronic kidney disease (KD) on hemodialysis. In some embodiments, the drug delivery device may contain or be used with ABP 798 (rituximab), a biosimilar candidate to Rituxan®/MabThera™, or another product containing an anti-CD20 monoclonal antibody. In some embodiments, the drug delivery device may contain or be used with a VEGF antagonist such as a non-antibody VEGF antagonist and/or a VEGF-Trap such as aflibercept (Ig domain 2 from VEGFR1 and Ig domain 3 from VEGFR2, fused to Fc domain of IgG1). In some embodiments, the drug delivery device may contain or be used with ABP 959 (eculizumab), a biosimilar candidate to Soliris®, or another product containing a monoclonal antibody that specifically binds to the complement protein C5. In some embodiments, the drug delivery device may contain or be used with Rozibafusp alfa (formerly AMG 570) is a novel bispecific antibody-peptide conjugate that simultaneously blocks ICOSL and BAFF activity. In some embodiments, the drug delivery device may contain or be used with Omecamtiv mecarbil, a small molecule selective cardiac myosin activator, or myotrope, which directly targets the contractile mechanisms of the heart, or another product containing a small molecule selective cardiac myosin activator. In some embodiments, the drug delivery device may contain or be used with Sotorasib (formerly known as AMG 510), a $KRAS^{G12C}$ small molecule inhibitor, or another product containing a $KRAS^{G12C}$ small molecule inhibitor. In some embodiments, the drug delivery device may contain or be used with Tezepelumab, a human monoclonal antibody that inhibits the action of thymic stromal lymphopoietin (TSLP), or another product containing a human monoclonal antibody that inhibits the action of TSLP. In some embodiments, the drug delivery device may contain or be used with AMG 714, a human monoclonal antibody that binds to Interleukin-15 (IL-15) or another product containing a human monoclonal antibody that binds to Interleukin-15 (IL-15). In some embodiments, the drug delivery device may contain or be used with AMG 890, a small interfering RNA (siRNA) that lowers lipoprotein(a), also known as Lp(a), or another product containing a small interfering RNA (siRNA) that lowers lipoprotein(a). In some embodiments, the drug delivery device may contain or be used with ABP 654 (human IgG1 kappa antibody), a biosimilar candidate to Stelara®, or another product that contains human IgG1 kappa antibody and/or binds to the p40 subunit of human cytokines interleukin (IL)-12 and IL-23. In some embodiments, the drug delivery device may contain or be used with Amjevita™ or Amgevita™ (formerly ABP 501) (mab anti-TNF human IgG1), a biosimilar candidate to Humira®, or another product that contains human mab anti-TNF human IgG1. In some embodiments, the drug delivery device may contain or be used with AMG 160, or another product that contains a half-life extended (HLE) anti-prostate-specific membrane antigen (PSMA)×anti-CD3 BiTE® (bispecific T cell engager) construct. In some embodiments, the drug delivery device may contain or be used with AMG 119, or another product containing a delta-like ligand 3 (DLL3) CAR T (chimeric antigen receptor T cell) cellular therapy. In some embodiments, the drug delivery device may contain or be used with AMG 119, or another product containing a delta-like ligand 3 (DLL3) CAR T (chimeric antigen receptor T cell) cellular therapy. In some embodiments, the drug delivery device may contain or be used with AMG 133, or another product containing a gastric inhibitory polypeptide receptor (GIPR) antagonist and GLP-1R agonist. In some embodiments, the drug delivery device may contain or be used with AMG 171 or another product containing a Growth Differential Factor 15 (GDF15) analog. In some embodiments, the drug delivery device may contain or be used with AMG 176 or another product containing a small molecule inhibitor of myeloid cell leukemia 1 (MCL-1). In some embodiments, the drug delivery device may contain or be used with AMG 199 or another product containing a half-life extended (HLE) bispecific T cell engager construct (BiTE®). In some embodiments, the drug delivery device may contain or be used with AMG 256 or another product containing an anti-PD-1×IL21 mutein and/or an IL-21 receptor agonist designed to selectively turn on the Interleukin 21 (IL-21) pathway in programmed cell death-1 (PD-1) positive cells. In some embodiments, the drug delivery device may contain or be used with AMG 330 or another product containing an anti-CD33×anti-CD3 BiTE® (bispecific T cell engager) construct. In some embodiments, the drug delivery device may contain or be used with AMG 404 or another product containing a human anti-programmed cell death-1(PD-1) monoclonal antibody being investigated as a treatment for patients with solid tumors. In some embodiments, the drug delivery device may contain or be used with AMG 427 or another product containing a half-life extended (HLE) anti-fms-like tyrosine kinase 3 (FLT3)×anti-CD3 BiTE® (bispecific T cell engager) construct. In some embodiments, the drug delivery device may contain or be used with AMG 430 or another product containing an anti-Jagged-1 monoclonal antibody. In some embodiments, the drug delivery device may contain or be used with AMG 506 or another product containing a multi-specific FAP×4-1BB-targeting DARPin® biologic under investigation as a treatment for solid tumors. In some embodiments, the drug delivery device may contain or be used with AMG 509 or another product containing a bivalent T-cell engager and is designed using XmAb® 2+1 technology. In some embodiments, the drug delivery device may contain or be used with AMG 562 or another product containing a half-life extended (HLE) CD19×CD3 BiTE®

(bispecific T cell engager) construct. In some embodiments, the drug delivery device may contain or be used with Efavaleukin alfa (formerly AMG 592) or another product containing an IL-2 mutein Fc fusion protein. In some embodiments, the drug delivery device may contain or be used with AMG 596 or another product containing a CD3× epidermal growth factor receptor vIII (EGFRvIII) BiTE® (bispecific T cell engager) molecule. In some embodiments, the drug delivery device may contain or be used with AMG 673 or another product containing a half-life extended (HLE) anti-CD33×anti-CD3 BiTE® (bispecific T cell engager) construct. In some embodiments, the drug delivery device may contain or be used with AMG 701 or another product containing a half-life extended (HLE) anti-B-cell maturation antigen (BCMA)×anti-CD3 BiTE® (bispecific T cell engager) construct. In some embodiments, the drug delivery device may contain or be used with AMG 757 or another product containing a half-life extended (HLE) anti-delta-like ligand 3 (DLL3)×anti-CD3 BiTE® (bispecific T cell engager) construct. In some embodiments, the drug delivery device may contain or be used with AMG 910 or another product containing a half-life extended (HLE) epithelial cell tight junction protein claudin 18.2×CD3 BiTE® (bispecific T cell engager) construct.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. A drug delivery device comprising: a housing; a drug container coupled to the housing, the drug container including a needle; a needle shield disposed at least partially over a distal end of the needle of the drug container; a removable cap coupled to the housing; and a needle shield remover coupled to the removable cap and the needle shield, such that uncoupling the removable cap from the housing removes the needle shield off the needle of the drug container, the needle shield remover comprising: a body having a tubular configuration with a first end and a second end, the body formed from a sheet of material having a first longitudinal edge opposing a second longitudinal edge; and a closure coupling the first and second longitudinal edges together to form the tubular configuration of the body, the closure comprising: a plurality of teeth extending laterally outwardly from the first longitudinal edge; and a plurality of grooves extending laterally inwardly into the sheet of material from the second longitudinal edge, the plurality of grooves being configured to receive the plurality of teeth to couple the first and second longitudinal edges together, wherein each of the plurality of teeth extends generally perpendicularly away from the first longitudinal edge; wherein each of the plurality of grooves extends along an axis at a non-perpendicular angle with respect to the second longitudinal edge, such that the plurality of teeth bend as each respective tooth enters a respective one of the plurality of grooves, a first plurality of barbs arrayed around a circumference of the body adjacent to the first end, the first plurality of barbs gripping the removable cap; and a second plurality of barbs arrayed around the circumference of the body adjacent to the second end, the second plurality of barbs gripping the needle shield, wherein the removable cap comprises a central wall and an annular wall disposed within the removable cap, wherein the first plurality of barbs is configured to grip the central wall, and wherein the annular wall is spaced outwardly from the central wall and configured to engage an outer surface of the first end of the body.

2. The drug delivery device of claim 1, wherein the needle shield remover is symmetrical about a horizontal plane extending through a midpoint of the body perpendicular to a longitudinal axis thereof.

3. The drug delivery device of claim 1, wherein axes of the plurality of grooves include the axis of each of the plurality of grooves, and the axes of the plurality of grooves are staggered to extend above or below a horizontal line extending between the first and second longitudinal edges.

4. The drug delivery device of claim 1, wherein the drug container is filled or pre-filled with a drug, and wherein the drug comprises one of: a drug containing a human IgG1 kappa antibody, a drug containing a small interfering RNA (siRNA) that lowers lipoprotein(a), efavaleukin alfa, evolocumab, and a drug containing a gastric inhibitory polypeptide receptor (GIPR) antagonist and a GLP-1R agonist.

5. The drug delivery device of claim 1, wherein each of the first plurality of barbs and second plurality of barbs extends within an opening of the body and include a distal end having laterally spaced pointed tips.

6. The drug delivery device of claim 1, wherein the first plurality of barbs and the second plurality of barbs extend inwardly into the body.

7. The drug delivery device of claim 1, wherein each of the plurality of teeth includes an associated cut-out portion configured to relieve stress within the material as a result of the plurality of teeth bending as each respective tooth enters the respective one of the plurality of grooves.

8. The drug delivery device of claim 7, wherein the associated cut-out portion is disposed on a side of each respective tooth that faces a direction of the non-perpendicular angle of the respective groove.

9. The drug delivery device of claim 1, wherein the sheet of material includes a sheet of metal having a thickness of less than 0.1 inches.

10. The drug delivery device of claim 1, wherein the central wall includes an outwardly protruding lip at a distal end thereof, and wherein the first plurality of barbs is configured to grip the removable cap under the outwardly protruding lip.

11. The drug delivery device of claim 10, wherein the central wall further includes an inwardly tapered portion adjacent to the lip to provide the first plurality of barbs access to an underside of the outwardly protruding lip.

12. A drug delivery device comprising: a housing; a drug container coupled to the housing, the drug container including a needle; a needle shield disposed at least partially over a distal end of the needle of the drug container; a removable cap coupled to the housing; and a needle shield remover coupled to the removable cap and the needle shield, the needle shield remover comprising: a body having a tubular configuration with a first end and a second end, the body formed from a sheet of metal having a first longitudinal edge opposing a second longitudinal edge; a closure coupling the first and second longitudinal edges together to form the tubular configuration of the body, the closure comprising: a plurality of teeth extending laterally outwardly from the first longitudinal edge; and a plurality of grooves extending laterally inwardly into the sheet of metal from the second longitudinal edge, the plurality of grooves being configured to receive the plurality of teeth to couple the first and second longitudinal edges together; a first plurality of barbs arrayed around a circumference of the body adjacent to the first end, the first plurality of barbs gripping the removable cap; and a second plurality of barbs arrayed around the circumference of the body adjacent to the second end, the second plurality of barbs gripping the needle shield, wherein the removable cap comprises a central wall and an annular wall disposed within the removable cap, wherein the central wall is configured to be gripped by the first plurality of barbs, and wherein the annular wall is spaced outwardly from the central wall and configured to engage an outer surface of the first end of the body.

13. The drug delivery device of claim 12, wherein the needle shield remover is symmetrical about a horizontal plane extending through a midpoint of the body perpendicular to a longitudinal axis thereof.

14. The drug delivery device of claim 12, wherein axes of the plurality of grooves include the axis of each of the plurality of grooves, and the axes of the plurality of grooves are staggered to extend above or below a horizontal line extending between the first and second longitudinal edges.

15. The drug delivery device of claim 12, wherein each of the first plurality of barbs and second plurality of barbs extends within an opening of the body and include a distal end having laterally spaced pointed tips.

16. The drug delivery device of claim 12, wherein the first plurality of barbs and the second plurality of barbs extend inwardly into the body.

17. The drug delivery device of claim 12, wherein each of the plurality of teeth includes an associated cut-out portion configured to relieve stress within the metal as a result of the plurality of teeth bending as each respective tooth enters the respective one of the plurality of grooves.

18. The drug delivery device of claim 12, wherein the central wall includes an outwardly protruding lip at a distal end thereof, and wherein the first plurality of barbs is configured to grip the removable cap under the outwardly protruding lip.

19. The drug delivery device of claim 18, wherein the central wall further includes an inwardly tapered portion adjacent to the lip to provide the first plurality of barbs access to an underside of the outwardly protruding lip.

20. The drug delivery device of claim 12, wherein the drug container is filled or pre-filled with a drug, and wherein the drug comprises one of: a drug containing a human IgG1 kappa antibody, a drug containing a small interfering RNA (siRNA) that lowers lipoprotein(a), efavaleukin alfa, evolocumab, and a drug containing a gastric inhibitory polypeptide receptor (GIPR) antagonist and a GLP-1R agonist.

* * * * *